(12) United States Patent
Hefti et al.

(10) Patent No.: US 7,713,477 B2
(45) Date of Patent: May 11, 2010

(54) SYSTEMS AND METHODS FOR MONITORING CHEMICAL AND BIOLOGICAL ACTIVITIES USING DIFFERENTIAL MEASUREMENTS

(76) Inventors: John J. Hefti, 2636 Fulton St., San Francisco, CA (US) 94118; Dean M. Drako, 320 Jane Dr., Woodside, CA (US) 94062

( * ) Notice: Subject to any disclaimer, the term of this patent is extended or adjusted under 35 U.S.C. 154(b) by 1790 days.

(21) Appl. No.: 10/799,000

(22) Filed: Mar. 11, 2004

(65) Prior Publication Data

US 2004/0170530 A1  Sep. 2, 2004

Related U.S. Application Data

(63) Continuation-in-part of application No. 10/064,392, filed on Jul. 9, 2002, now abandoned.

(60) Provisional application No. 60/375,668, filed on Apr. 26, 2002.

(51) Int. Cl.
| | |
|---|---|
| G01N 15/06 | (2006.01) |
| G01N 27/00 | (2006.01) |
| G01N 25/08 | (2006.01) |
| G01N 25/18 | (2006.01) |
| G01N 27/30 | (2006.01) |

(52) U.S. Cl. ............ 422/68.1; 422/76; 422/82.01; 422/82.02; 422/82.03; 435/6; 435/7.1; 436/149; 436/150

(58) Field of Classification Search ............ None
See application file for complete search history.

(56) References Cited

U.S. PATENT DOCUMENTS 3,941,563 A   3/1976 Saltzman (Continued)

FOREIGN PATENT DOCUMENTS

EP   0 275 617   7/1988

(Continued)

OTHER PUBLICATIONS

Sadik et al, Differential Impedance Spectroscopy for Monitoring Protein Immobilization and Antibody-Antigen Reactions, Analytical Chem, vol. 74, No. 13, May 2002, pp. 3142-3150.

(Continued)

*Primary Examiner*—Jill Warden
*Assistant Examiner*—Neil Turk
(74) *Attorney, Agent, or Firm*—Clifford B. Perry

(57) ABSTRACT

A system operable to monitoring bio/chemical activities includes a first measurement probe, a second measurement probe and a comparator. The first measurement probe is operable to interrogate one or more physical properties of a sample at a first location of the sample, and to output, in response, a first measurement signal. The second measurement probe is operable to interrogate one or more physical properties of the sample at a second location of the sample, and to output, in response, a second measurement signal. The comparator is coupled to receive the first and second measurement signals, the comparator configured to output a difference signal comprising the difference between the first and second measurement signals, the difference signal corresponding to the difference in one or more bio/chemical activities occurring at the first location of the sample relative to the second location of the sample.

15 Claims, 19 Drawing Sheets

U.S. PATENT DOCUMENTS

| | | | |
|---|---|---|---|
| 3,999,047 A | 12/1976 | Green | |
| 4,072,576 A * | 2/1978 | Arwin et al. | 435/4 |
| 5,004,583 A * | 4/1991 | Guruswamy et al. | 422/58 |
| 5,192,507 A | 3/1993 | Taylor et al. | |
| 5,212,988 A | 5/1993 | White et al. | |
| 5,267,985 A | 12/1993 | Shimada et al. | |
| 5,554,339 A | 9/1996 | Cozzette et al. | |
| 5,597,534 A * | 1/1997 | Kaiser | 422/82.02 |
| 5,837,115 A | 11/1998 | Austin et al. | |
| 5,837,200 A | 11/1998 | Diessel et al. | |
| 5,907,016 A | 5/1999 | Velander et al. | |
| 5,910,286 A | 6/1999 | Lipskier | |
| 5,952,173 A | 9/1999 | Hansmann et al. | |
| 5,955,028 A | 9/1999 | Chow | |
| 5,965,410 A | 10/1999 | Chow et al. | |
| 6,143,574 A | 11/2000 | Karlsson et al. | |
| 6,171,865 B1 | 1/2001 | Weigl et al. | |
| 6,241,950 B1 | 6/2001 | Veelenturf et al. | |
| 6,274,089 B1 | 8/2001 | Chow et al. | |
| 6,455,000 B1 | 9/2002 | Conrad et al. | |
| 6,534,012 B1 | 3/2003 | Hazen et al. | |
| 6,825,655 B2 | 11/2004 | Michole et al. | |

FOREIGN PATENT DOCUMENTS

| | | |
|---|---|---|
| EP | 1 211 507 | 6/2002 |
| GB | 1 298 245 | 11/1972 |
| JP | 56 046450 | 7/1981 |
| WO | WO 0022434 | 4/2000 |
| WO | WO 0072020 | 11/2000 |
| WO | WO 0223161 | 3/2002 |

OTHER PUBLICATIONS

Courtesy ISR of PCT/US04/12614 dated Jan. 24, 2005.
Courtesy supplementary European search report for corresponding EP application 04 750 558.

* cited by examiner

SYSTEMS AND METHODS FOR MONITORING CHEMICAL AND BIOLOGICAL ACTIVITIES USING DIFFERENTIAL MEASUREMENTS

CROSS REFERENCE TO RELATED APPLICATIONS

This is a continuation-in-part of prior U.S. patent application Ser. No. 10/064,392, filed Jul. 9, 2002, which claims the benefit of U.S. Provisional Application No. 60/375,668, filed Apr. 26, 2002, each application herein incorporated by reference in its entirety for all purposes.

BACKGROUND

Biologic systems and complex chemical processes, such as biochemical pathways, cellular activities, synthetic organic processes, and molecular interactions (collectively referred to bio/chemical activity herein) pose considerable challenges to scientists interested in directly monitoring activities. Such systems usually are rather complex, existing in environments where a number of differing activities are occurring simultaneously, and are thus noisy. Currently, there are a number of general techniques routinely used for detecting biochemical phenomena [David Freifelder, *Physical Biochemistry*, 1982, second edition, W. H. Freeman & Co., New York], most of which employ techniques in which one or more of the constituents of the system is labeled in some fashion; often times, these labeling approaches show whether or not a particular event has occurred, such as the binding of one molecule to another, or altered activity of a particular step in a biochemical pathway [D. E. Koshland, 1970, *The Molecular Basis for Enzyme Regulation*, in *The Enzymes*, P. Boyer, Ed., 341-396, Academic Press]. A very limited number of techniques utilize the measurement of properties which directly measure some physiologic property of a system, or do not require the attachment of a label. However, in these cases, only a very limited amount of information is available, and in most cases, the techniques are difficult to carry out, and thus the throughput is extremely limited.

Many chemical and biological systems are amenable to direct physiologic detection, such as through the use electronic measurement techniques. Many activities of interest in these areas result in direct or indirect changes in the electromagnetic properties of the system. Indeed, numerous methods have been developed in which various electronic and electromagnetic properties of the system are monitored, and changes therein are correlated to the presence or absence of one or more activities. Electronic and electromagnetic monitoring has many advantages over other methods of detection: Electronic systems can be made very small, can be scaled to very high densities and/or large parallel systems, can be manufactured very cheaply, and are highly durable and impervious to environmental factors.

In order for a given system to be amenable to electronic and electromagnetic monitoring, as is currently practiced in the art, the system, and changes therein, must produce a large enough signal to be measured. To be more precise, the signal needs to be detectable over the background noise which is almost always present in such systems. This poses many problems for the general application of these techniques to chemical and biologic systems, as there often is a high level of inherent noise, and small changes due do specific chemical or biologic activities are therefore not detectable. For example, many systems are comprised largely of water and ionic species, both of which exhibit large changes in their electrical properties as a function of temperature. Small changes in ambient temperature produce changes in the electrical properties of the system being studied, thus rendering the signal effectively undetectable. Another relevant example is the detection of s specific activity in a complex mixture, such as a suspension of biologic cells or tissues; there are multiple activities on-going at any given time, so the detection of a specific activity is very challenging, at least if its signal is not easily separated from all of the other signals in the system.

The have been many attempts to address the problem of specificity and noise in electronic detection modalities. In many cases, the signal measured electromagnetically is derivative of the activity desired to be monitored. In most of these cases, the specific activity or activities it is desired to detect is directly or indirectly coupled to a system which effectively amplifies the signal, and thus makes it detectable. Examples of this include enzymatic processes, in which a particular analyte is modified in some way that renders it more easily detected. One such example is the use of the enzyme glucose oxidase to change an uncharged species (glucose) into charged species (gluconic acid), resulting in a change in the conductance of the medium in which the glucose resides. The change in conductance can then be detected using conventional instruments for the measurement of electrical conductivity. Other approaches involve altering the oxidation-reduction characteristics of a given analyte, creating dense monolayers of specific chemistries on conductive surfaces, in order to alter the contact resistance and/or reactance as a marker for activity. Yet another class of approaches is the creation of ultra-sensitive measurement modalities, for the purpose of directly measuring altered electrical and/or dielectric properties which result from some specific activity in the system.

Each of the above-mentioned approaches has limitations. In systems where some form of amplification needs to take place, the added burden of incorporating a mechanism for amplification is time consuming, incurs costs, and in many cases is not possible. In cases where ultra-sensitive measurement systems are used, there are often considerable costs, and often the size and throughput of the system makes it unsuitable for many applications.

Thus, although electronic detection has found utility in biological, chemical, medical, and industrial applications, there exist significant limitations which prevent larger utility. Accordingly, there is need for a system operable to measure, monitor and detect biologic and chemical activities using electronic and electromagnetic measurement modalities.

SUMMARY OF THE INVENTION

The present invention provides systems and methods for monitoring biologic and chemical activities using differential measurements. These systems can be utilized in a wide range of applications, from large-scale industrial monitoring to ultra-small microfluidic process monitoring and detection.

In one embodiment, a system operable to monitoring bio/chemical activities includes a first measurement probe, a second measurement probe and a comparator. The first measurement probe is operable to interrogate one or more physical properties of a sample at a first location of the sample, and to output, in response, a first measurement signal. The second measurement probe is operable to interrogate one or more physical properties of the sample at a second location of the sample, and to output, in response, a second measurement signal. The comparator is coupled to receive the first and second measurement signals, the comparator configured to output a difference signal comprising the difference between the first and second measurement signals, the difference signal corresponding to the difference in one or more bio/chemical activities occurring at the first location of the sample relative to the second location of the sample.

Additional embodiments of the invention are described and shown in the following drawings and detailed description.

Figure 1A:
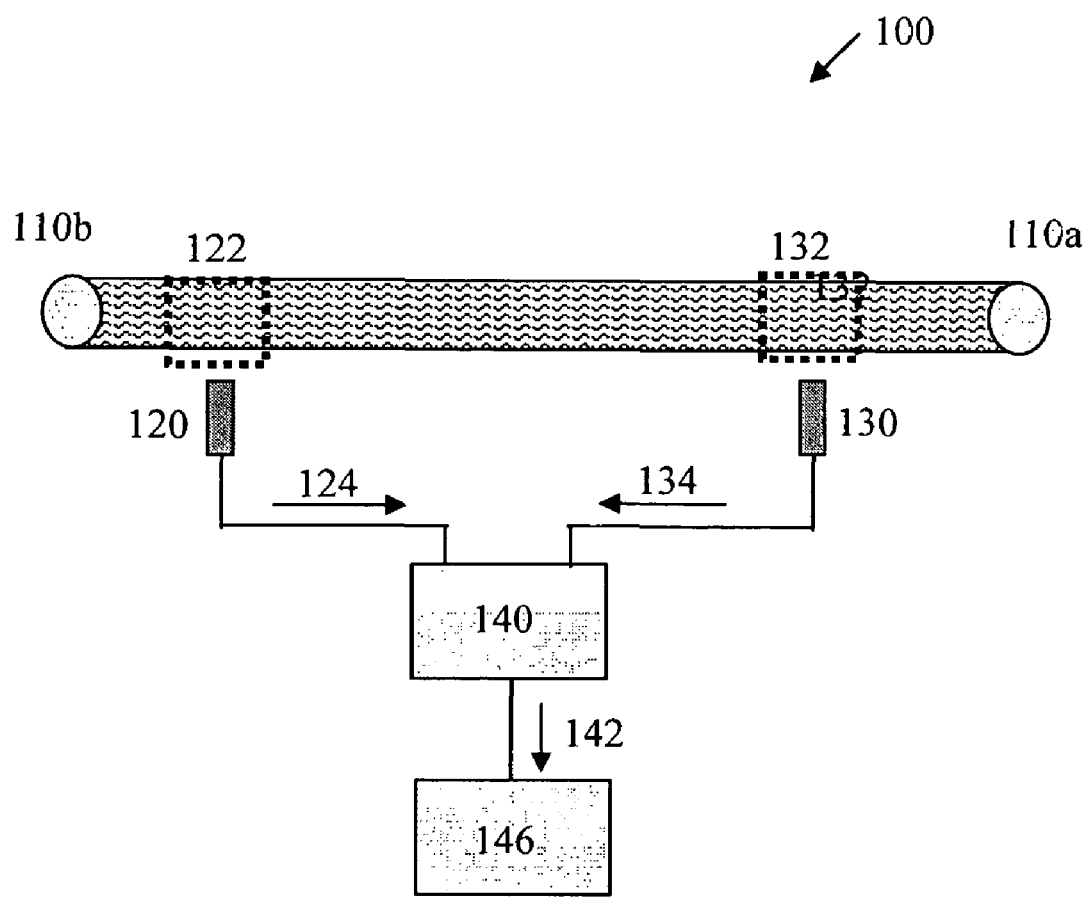
FIG. 1A illustrates a first embodiment of a differential measurement system for monitoring bio/chemical activities in accordance with the present invention.

For clarity and convenience, previously identified components and features retain their reference numerals in subsequent illustrations.

DETAILED DESCRIPTION OF SPECIFIC EMBODIMENTS

I. Definitions

As used herein, the term "bio/chemical activity(ies)" refers to the biologic or chemical response of a biologic or chemical species Exemplary embodiments of bio/chemical activities include pairwise binding of two biologic or chemical species such as occur in the binding of a small molecule to a protein receptor; the binding or interaction of three or more biologic or chemical species, such as occur in the binding of protein complexes; more complex serial or parallel interactions of any number of biologic or chemical species, such as occur in biochemical pathways for the metabolic and signaling activities in biologic systems; chemical binding and reactions, such as enzymatic catalysis, oxidation-reduction reactions, chemical signaling though hormones or chemokines, and other types of chemical reactions; other types of biologic activities, such as neuronal signaling via membranous ion channel opening and closing; anabolic activities such as protein synthesis and expression, nucleic acid synthesis and expression; assembly and fabrication of more complex biologic structures such as the cytoskeleton, membrane-resident protein association and transport, cellular and organelle replication; and morphologic activities, such as storage and transport of biologic or chemical species, protein expression and secretion, intercellular communications though diffusion or transport of biologic or chemical species, cellular motility and intercellular interactions, and the like These are only a few of the exemplary embodiments within the scope of the present invention. The phrase "monitoring bio/chemical activity(ies)" is used to describe: (i) the detection of either the presence or absence of one or more biochemical activities, (ii) quantitating the level of one or more bio/chemical activities occurring, and/or (iii) quantitating the rate of change in one or more bio/chemical activities occurring.

As used herein, "bio/chemical species" refers to any chemical or biologic structure, including, but not limited to: small molecules such as organic and inorganic chemical compounds, proteins and peptides, lipids, nucleic acids, polysaccharides, ionic species, cofactors, synthetic compounds of molecular weight less the 500D intended for therapeutic purposes, other endogenous structures such as hormones, signaling peptides, neurotransmitters; larger biologic structures such as proteins, lipids, polysaccharides, antigens and antibodies, protein receptors and signaling structures, nucleic acids, larger proteins and protein complexes such as ion channels, other membranous protein structures, cell membranes, intracellular structures such as endoplasmic reticulum and organelles, prokaryotic ad eukaryotic cells, yeast and fungi, ordered and random populations of cells, tissues comprised of cells obtained from living and non-living organisms, and the like.

As used herein, the term "reactive constituent" refers to a compound which is known, or suspected of being reactive with the bio/chemical species, defined above. For example, in an embodiment in which the bio/chemical species consists of a molecular structure, the reactive constituent may comprise a molecule which is known or suspect of having a binding affinity thereto. In an embodiment in which the bio/chemical species consists of a cellular structure, the reactive constituent may comprise a small molecule which binds to the cell, or another constituent which is metabolized or otherwise alters the cells function. Examples of the forgoing include, but are not limited to: molecules within the cell which are involved with metabolic activities, such as nutrient catabolic or anabolic processes; intermediate molecular constituents in a biochemical pathway, including regulatory molecules and signaling molecules; signaling molecules, such as neurotransmitters and hormones, as well as other peptidic and non-peptidic organic compounds; small molecules intended for therapeutic purposes, such as drugs and other molecules known or suspected of being biochemically active in a given cell population, and the like.

As used herein, the term "reactive center" refers to a region within the sample where one or more chemical and/or biological processes occur. Generally, reactive center refers to a localized region within a larger system, in which one or more specific bio/chemical activities may take place, optionally by design.

As used herein, the term "physical property(ties)" refers to one or more physical characteristics of the bio/chemical species, as defined previously, which result from the bio/chemical species' physical and/or chemical structure, and changes thereof. Exemplary physical properties of a sample include the sample's electrical properties, such as conductivity, permittivity, resistivity, permeability, and the like. Additional exemplary physical properties further include optical properties such as polarization, dispersion, or opaqueness or transparency to a particular wavelength of light. Other exemplary physical properties may further include radiometric properties, colorimetric properties, chemical properties such as enzymatic activities, electrochemical activities, or synthetic activities, and mass and/or charge properties such as molecular weight, diffusion, evaporation, and mass-to-charge ratio.

As used herein, the terms "signal path" and "transmission line" refers to a structure which is designed to support the propagation of a signal. A non-exhaustive list of examples includes: metals and other materials which are capable of conducting either direct current or alternating current electromagnetic signals; two conductor structures operable to support the propagation of transverse electromagnetic (TEM) waves, standard or dielectric waveguides, such as those used for the transport of microwave and millimeter wave frequencies, fiber-optic structures for conveying optical wavelength signals; fluid channels which contain conducting fluids, such as aqueous based buffers which include free ions capable of carrying electric charges; and the like. A signal path may consist of a plurality of materials and interfaces therebetween, and may consist of complex connective topologies, or simple point-to-point connections.

As used herein, the term "electrical signal(s)" or electrical measurement(s)" refers to a time-varying (ac) or time-invariant (dc) signal, the former operating over at any useful and measurable frequency. In one embodiment, a time-varying electrical signal extends over the Low frequency (LF) to millimeter-wave frequency range (1 KHz-100 GHz).

As used herein, the term "optical signal(s)" refers to a signal within the optical spectrum, e.g., in the range of 7000 to 4000 Angstroms, though longer wavelengths such as near infrared, mid-infrared, and far infrared, and shorter wavelengths such as ultraviolet and x-ray wavelengths, may also be referred to as optical signals.

As used herein, the term "coupled" refers to the condition in which the described elements permit a signal to be communicated therebetween. As used in the art of electrical/electronic patents most commonly, "coupling" may occur between directly contiguous structures, as well as non-contiguous structures having one or more intervening elements, structures or fluids. Further as known in the art of electronics, "coupling" may occur either through the direct contact of the described elements, or between elements not in physical contact through electrostatic, magnetostatic, or electromagnetic coupling. Exemplary embodiments of coupling in the present invention occur between directly-connected circuit elements, between a measurement probe and the sample, between two or more measurement probes (e.g., through the sample, other intervening structure, etc.), or between any two items in which the transference of a signal from one to the other is described.

As used herein, the term "null" refers to the minimum value of a differential measurement. An ideal null is a value of zero in a given differential measurement, but often refers to the best achievable difference, as is well-known in the art. A null may be used herein to describe an initial state of a given system, in which the value of a differential measurement is a minimum, and against which other values may optionally be compared.

II. General Overview

Advances in small scale fabrication techniques, both electronic (e.g. semiconductor processing, micro-electromechanical systems or MEMS, as well as lithography) and non-electronic (e.g. microfluidics), now allow the manufacture of structures whose typical dimensions are roughly comparable to many structures of biologic interest, such as cells, cell membranes, organelles, micro-beads with various biologically relevant structures attached to them, and larger molecules. In addition, these fabrication techniques are highly reproducible, and can be used to construct geometries which are very regular and easily amenable to modeling and simulation of the behavior of systems contained therein.

The electronic embodiments of these structures are capable of addressing and conveying measurement signals to very small spatial regions for sample interrogation, as well as to create topologically complex circuits of very high density. Application of micro-fabrication techniques enables the capture and management of very small fluid samples in microfluidic structures, in which both dissolved and non-dissolved biologic and chemical constituents may be manipulated and tested. In such an environment, the sample's physical properties such as conductivity, reactance, impedance, optical, colorimetric and spectral properties, and the like, can be used to monitor the sample's bio/chemical activities, as the sample's physical properties are highly dependent upon the bio/chemical activities occurring therein. By creating a well-controlled environment within which the sample can be interrogated and subsequently monitoring one or more of the sample's physical properties through the measurement process, the presence, absence, quantity and/or rate of change of one or more bio/chemical activities can be ascertained. This method can be performed in a serial fashion on a single sample whereby the sample is repeatedly exposed to a particular reactive component and certain bio/chemical activities monitored after each exposure, or in a parallel fashion, whereby the biochemical activity of a first sample (e.g., a reference sample having known bio/chemical activity) is compared against the unknown bio/chemical activity of a second sample (e.g., a test sample). Each of these methods can be used to obtain a depth of understanding about the behavior of a whole range of biologic, chemical, and molecular systems. In particular, these processes can be used to provide platforms in which complex biologic and chemical systems can be simulated, prepared, managed, detected, and monitored, all in a highly parallel manner. The result is a collective ability to carry out very complex experiments on biologic and chemical systems, monitor the progress and conditions of the experiment, and to measure useful data on a variety of experimental parameters.

Differential Measurement Platform

As discussed above, the measurement processes employed in conventional systems are typically limited in their precision and accuracy by variables within the measured system which alter the measured value, but which are not of interest to be measured. For example, in fluid samples which contain many resident molecular constituents, the overall conductivity of the sample is determined by the electrical properties of an ensemble of the molecules within the sample. If one then desires to use conductivity of the sample as an indicator of a specific interaction or process, for example, the interaction between one molecular species and a second molecular species, then it is necessary that the change in conductivity due to the specific interaction or process be measurable within the overall conductivity of the sample. Another relevant example is the measurement of cellular activities in biological samples. Often times one is interested in detecting the activities of a single pathway within a cell, but the nature of living cells is to have many active pathways. Thus, it is often times very challenging to separate the signal which derives from the pathway of interest from the signals which derive from all of the other pathways. In many cases, the specific effect is too small to be detected; or in more technical terms, the signal-to-noise ratio is too low to enable detection. The present invention overcomes these short-comings through the use of a differential measurement platform in which two or more measurements of the sample's physical properties are taken and the measurements' relative difference obtained. This relative difference may exhibit a high degree of 'common mode rejection', which is to say that activities of 'modes' which are common to both samples do not show up in the signal, and thus only signals which represent differing activities are detected.

FIG. 1A illustrates a first embodiment of a differential measurement system 100 for monitoring bio/chemical activities in accordance with the present invention. The monitoring system 100 includes a sample chamber 110, at least two measurement probes 120 and 130, and a comparator 140. The sample chamber 110 includes inlet port 110a for receiving the sample and an outlet port 110b for dispensing. The sample may be provided using any apparatus capable of delivering the appropriate sized sample to the chamber 110, such as a syringe pumps, droplets, pipettes, and the like. The sample chamber 110 may comprise a channel or a partially or completely enclosed structure formed from a variety of materials. For example, the sample chamber may comprise a microfluidic channel, a channel formed in a monolithic photolithography or injection molding process, or a well configuration in which one portion of the chamber is open to the environment.

The monitoring system 100 further includes at least two measurement probes 120 and 130 coupled to the sample at respective first and second locations 122 and 132, each probe 120 and 130 configured to interrogate the sample at its respective location, and to output respective measurement signals 124 and 134. The measurement probes 120 and 130 are coupled to the sample either directly (in direct contact with the sample), or indirectly (e.g., optically or electromagnetically coupled through air, or an intervening material). Further, each measurement probe may be configured to employ any particular signal means to interrogate the sample. For example, the measurement probes 120 and 130 may comprise radio frequency probes operable to illuminate the sample with one or more signals within the radio frequency range, each probe operable to detect amplitude and phase of a resultant signal after it interacts with the sample at its respective location. Alternatively, the probes 120 and 130 may comprise a laser operable to illuminate the sample with one or more signals in the optical spectrum, the probes operable to detect intensity, dispersion, or wavelength of the resultant light signal after interaction with the sample at the respective location. These examples are only illustrative, and the reader will appreciate that measurement probes using other types of signals may also be used in alternative embodiments under the present invention.

The monitoring system 100 further includes a comparator 140 operable to receive the measurement signals 124 and 134 from measurement probes 120 and 130, respectively, and to output, in response, a difference signal 142 corresponding to the difference between the measurement signals 124 and 134. The comparator 140 may comprise a variety of devices operable to perform the difference operation. For example, when the measurement signals are provided as electronic signals, the comparator may consist of a differential amplifier having two opposite polarity inputs for receiving the two measurement signals, the differential amplifier providing an output signal corresponding to the difference between the measurement signals 124 and 134. Other devices having the aforementioned functionality may be used in alternative embodiments.

The difference signal 142 is subsequently provided to a measurement device 146 which, based upon the characteristics of the difference signal, determines the presence, absence, level and/or rate of change in the bio/chemical activity. For example, the measurement device may comprise a voltmeter operable to measure the magnitude of the difference signal, the value of which indicates the presence or absence of a particular bio/chemical activity. In another embodiment, the measurement device may consist of a unit operable to record the time rate of change of the difference signal (e.g., the voltage magnitude-v-time), the time rate of change response being indicative of the level of bio/chemical activity occurring. These examples are only illustrative, and the reader will appreciate that other measurement devices can be used in alternative embodiments under the present invention. Further, the system may include a correlator (not shown) coupled to receive the difference signal and which stores the aforementioned characteristics of the previously-obtained difference signals, each of which has a known bio/chemical activity associated therewith. The characteristics of these stored difference signals can then be compared against to the presently measured difference signal to determine bio/chemical activity in the presently measured sample.

The monitoring system of FIG. 1A can be used to detect a wide range of bio/chemical activities, such as binding events and the activities of biological cells and tissues. Monitoring this type of bio/chemical activity could be accomplished by preparing the surface of one measurement probe to have a high binding affinity with a sought analyte, while preparing the surface of the other measurement probe to have a low binding affinity to the same analyte. The measurement probes are then contacted with a reference sample and the reference sample interrogated to obtain a set of reference measurements 124 and 134 (e.g., taking s-parameter measurements). Subsequently, a test sample suspected of containing a particular analyte is introduced into the sample chamber and contacts both measurement probes 120 and 130. If the suspected analyte is contained within the test sample, it will bind to the surface of one of the measurement probes with a higher affinity that the other, and as a result, the probes 120 and 130 will produce different measurement signal 124 and 134, the difference of which will be detectable (above the difference measured from the reference measurements), the difference indicating the presence of binding activity in the sample. Of course, an alternative arrange could be undertaken in which a complete bound protein structure is immobilized on the surface of one measurement probe, and only the protein's binding partner is immobilized on the surface of the other probe. In such an instance, the second probe's take up of the binding partner from the test sample will serve to produce substantially equivalent first and second measurement signals 124 and 134, and thus in this case their difference would converge to zero when the sought binding event is detected.

Figure 1B:
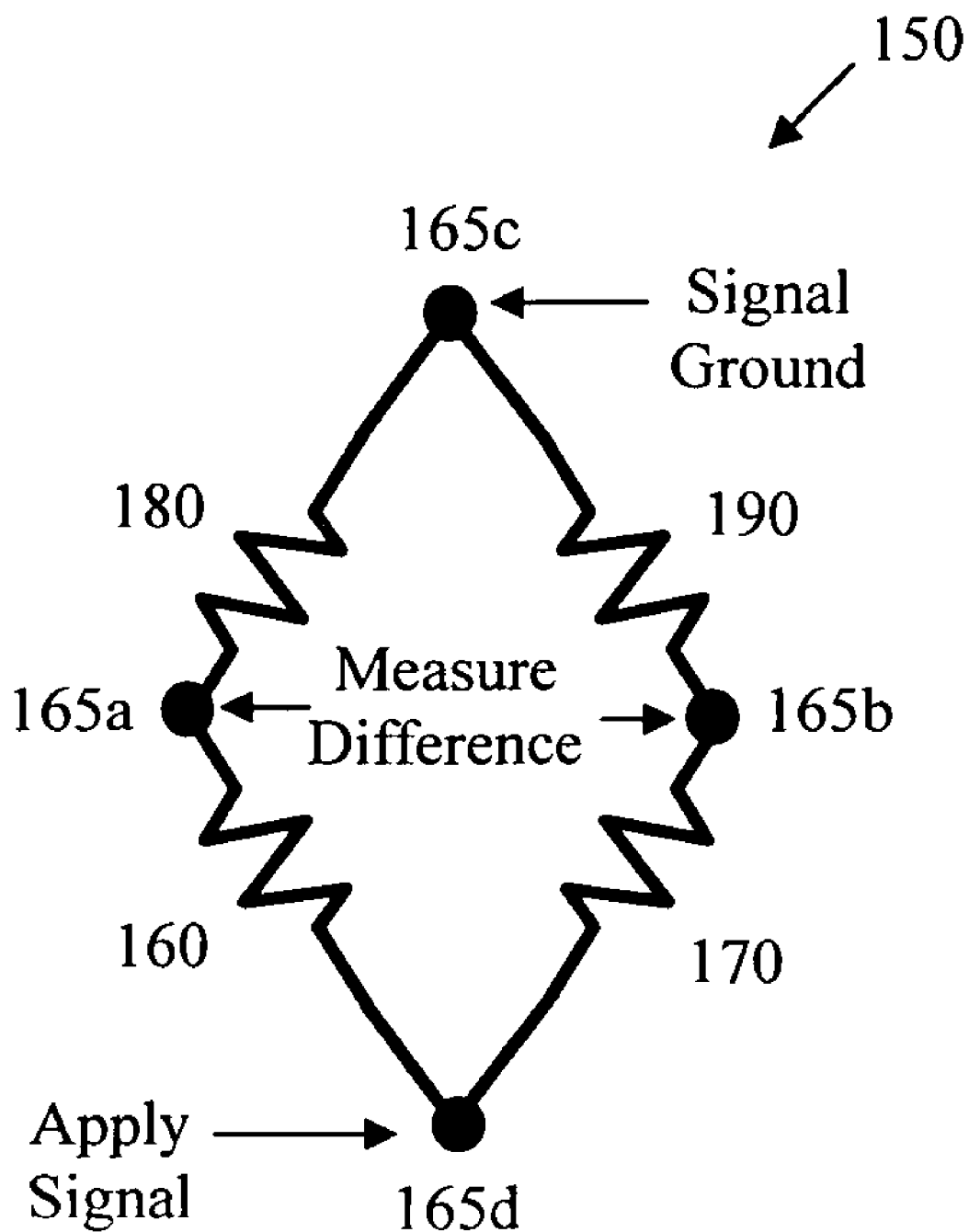
FIG. 1B illustrates a second embodiment of a differential measurement system for monitoring bio/chemical activities in accordance with the present invention.

Another type of differential measurement system useful in monitoring bio/chemical activities is the bridge circuit, such as the Wheatstone bridge circuit 150 shown in FIG. 1B. The bridge 150 includes reference elements 160, 170, 180 and 190, all shown as resistors as an example. The reference elements 160-190 make up two parallel circuits, such that in the absence of any differences between them within the bridge circuit, the voltage at symmetric points is equal. When the value of one reference element is changed, a voltage appears. For example, suppose a voltage is applied at 165*d*, which is common to both arms of the bridge. A first set of resistors 160 and 170, ideally of equal value, drop the applied voltage by a certain amount. A second set of resistors 180 and 190 drop the remaining voltage to a common ground. If the pair of resistors 160 and 170 are of equal value, and the pair of resistors 180 and 190 are of equal value, then the voltage drop across the midpoints 165*a* and 165*b* of the bridge is zero. However, if any one resistor differs in value from its partner, there will result a voltage drop across the midpoints. Further, the magnitude of this voltage drop will reveal the magnitude of the value of the unknown resistor, if the values of the other three resistors are known. Thus, very precise and accurate measurements of an unknown resistance can be made, simply by choosing known values for three of the resistors, applying a voltage and measuring the voltage difference across the midpoint of the bridge.

Bridge configurations are also useful to detect a relative change in a previous condition, and not necessary the magnitude of the change. For example, when using biosensors of chemical sensors to detect the presence of a particular antigen, the corresponding antibody may be immobilized on electrodes arranged in the bridge circuit configuration described above. In this case, the binding of antigen to the immobilized antibodies will alter the electromagnetic properties of the circuit element, and thus change the effective circuit parameters of the bridge circuit. This change in the circuit parameters could be measured absolutely. However, in many cases it may only be desired to determine if binding of antigen to antibody has occurred, not the absolute change in the circuit parameter due to binding. In such an instance, it would be sufficient to detect the relative change in the circuit parameter, without knowing the absolute value of this parameter, around which the measured value is changing.

III. Exemplary Embodiments of the Differential Signal Monitoring System

Further detailed embodiments of the differential signal monitoring system in accordance with the present invention are now presented below. The monitoring system may be constructed in either of the architectures shown in FIGS. 1A and 1B, as are illustrated below. Further, the detailed exemplary embodiments are presented in two categories of a single sample monitoring system (FIGS. 2A-C) and a multi-sample monitoring system (FIGS. 3A-G). The delineation between single and multiple sample monitoring systems is provided in order to illustrate the different applications in which either system may be used, as a single sample or multiple sample system may be more convenient, depending upon the application and/or specific bio/chemical activity monitored. No inference should be made that one type of system excludes components or features found in the other. Indeed, many of the systems employ the same or similar components and features.

Single Sample Monitoring Systems

Several embodiments of a single sample monitoring system are now provided, each system being configurable in either of the differential signal architectures of FIG. 1A or 1B. The single sample monitoring system may be preferred over the multiple sample system in certain applications, for example, when one seeks to test a particular sample for a range of different bio/chemical activities, for example, through the measurement of diffusion properties of structures within the sample. Other applications of a single sample monitoring system include, but are not limited to: detecting and quantitating cellular motility and migration rates, as occurs for example during chemotaxis; detecting and quantitating cell growth and proliferation, as occurs in response to various growth factors; the creation and/or alteration of concentration gradients of one or more analytes within the sample, as occurs during the secretion and uptake of signaling molecules and nutrients. The reader will appreciate that the single sample monitoring system is not limited exclusively to making the aforementioned measurements, and that it may be employed to monitor any bio/chemical activity.

Figure 2A:
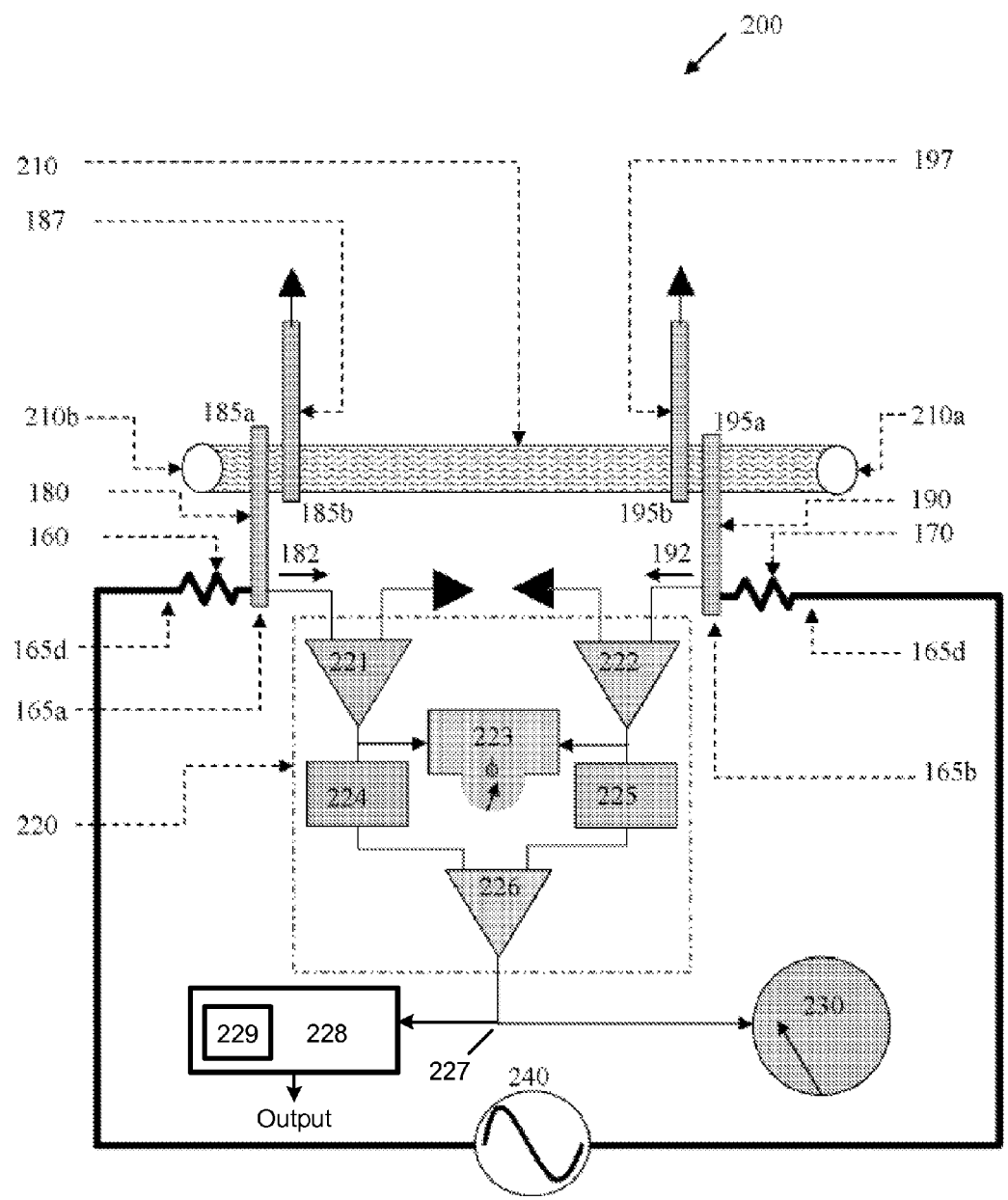
FIG. 2A illustrates a first embodiment of a single sample monitoring system in accordance with the present invention.

FIG. 2A illustrates a system 200 for monitoring bio/chemical activities within a single sample in accordance with one embodiment of the present invention, with previously identified features retaining their reference numerals. The system 200 is based upon the bridge circuit architecture shown in FIG. 1B in which circuit elements 160, 170, 180 and 190 make up the bridge circuit. The system 200 further comprises a sample chamber 210, a comparator 220, a difference meter 230, and a signal source 240.

As shown, the bridge circuit components 160 and 170 each comprise resistors, and components 180 and 190 comprise first and second measurement probes. The first measurement probe 180 is coupled (directly to the sample by contact or indirectly through an intervening material or gap) to the sample at a first location 185*a*, and the second measurement probe 190 is coupled (directly or indirectly) to the sample at a second location 195*a*. Each probe 180 and 190 is configured to measure one or more physical properties of the sample and to output a measurement signal corresponding thereto. For example, the measurement probes 180 and 190 may be configured to measure the sample's electrical properties (conductivity, impedance, permittivity, permeability, etc.), optical properties (polarization, opaqueness/transparency or dispersion at a predefined wavelength, etc,), chemical properties (enzymatic activities, electrochemical activities, or synthetic activities), or mass and/or charge properties (molecular weight, diffusion, evaporation, and weight-to-charge ratio). The system 200 further includes a first signal ground 187 coupled to the sample at a third location 185*b* proximate to the first measurement probe 180, and a second signal ground 197 coupled to the sample at a fourth location 195*b* proximate to the second measurement probe 197. In a particular embodiment described below, the first and second measurement probes and their corresponding signal grounds comprise transmission line structures, a portion of which includes immobilized antibodies attached thereto. The measurement probes 180 and 190 may comprise any structure suitable to support the propagation of the measurement signal, a few examples being wire, metal traces lithographically fabricated, optical fibers and/or waveguides, and the like.

The system 200 further includes a sample chamber 210 having inlet port 210*a* for receiving the sample and an outlet port 210*b* for dispensing. The sample may be provided using any apparatus capable of delivering the appropriate sized sample to the chamber 210, such as a syringe, pumps, droplets, pipettes, and the like. The sample chamber 210 may comprise a channel or completely enclosed closed structure formed from a variety of materials. For example, the sample chamber may comprise a micro-fluidic channel, or a channel formed in a monolithic photolithography or injection molding process, or a well configuration in which one portion of the chamber is open to the environment.

The system 200 further includes a comparator 220 operable to receive measurement signals 182 and 192 from measurement probes 180 and 190, respectively, and to output, in response, a difference signal 227 corresponding to the difference between the measurement signals 182 and 192. In the particular embodiment shown, the comparator 220 includes first and second differential amplifiers 221 and 222, a phase meter 223, optional first and second DC converters 224 and 225, a third differential amplifier 226, and a difference meter 230. An input of each of the first and second differential amplifiers 221 and 222 are connected to nodes 165$a$ and 165$b$, the other input connected to ground (ac and/or dc) potential. The outputs of the first and second differential amplifiers are coupled to the phase meter 223 operable to detect a relative difference in the phase between output signals of the first and second differential amplifiers. Optional DC converters 224 and 225 convert the differential amplifier output signals to DC-formatted signals. Exemplary embodiments of the DC converter circuit include: integrator circuits (such as resistor-capacitor circuits), analog-to-digital converters, root-mean-square voltage converters, averaging circuits, sample-and-hold circuits, digital sampling circuits, and the like. In embodiments in which the measurement signals 182 and 192 are DC-formatted, the DC converters can be omitted. The DC-formatted signals are then supplied to the third differential amplifier 226, which, in response, produces a difference signal 227. The difference signal 227 is input to the difference meter 230 which indicates the relative difference in the measurement signals 132 and 142. Optionally, the system may include a correlator 228 coupled to receive the difference signal and which stores (e.g., using a memory element 229) characteristics of the previously obtained difference signals, each of which has a known bio/chemical activity associated therewith. The characteristics of these stored difference signals (the difference signal's magnitude, phase, time rate of change, etc.) can then be compared against to the presently measured difference signal to determine bio/chemical activity in the presently measured sample. An output signal is provided which indicates the closest matching stored difference signal, that difference signal having a known bio/chemical activity associated therewith.

A signal source 240 is used to apply a signal at nodes 165$d$, which, through the dividing actions of resistors 160 and 170 and responses of measurement probes 180 and 190, produce the measurement signals 182 and 192. The signal source is optionally filtered to exclude effects from standard AC line ripple, or the power is optionally is provided by a DC source, such as a battery. While the monitoring system has been illustrated using electrical signals to monitor bio/chemical activities, other measurement modalities may be employed in alternative embodiments. For example, a photonic-based monitoring system may be used to monitor the bio/chemical activities of a sample by means optically interrogating the sample and measuring corresponding optically-based physical properties of the sample such as reflection, transparency, polarization, dispersion and the like. In such a system, the signal source 240 may comprise a laser, resistors 160 and 170 may comprise optical attenuators, and measurement probes 180 and 190 may be opto-electronic detectors. Similarly, those skilled in the art will appreciate that other systems such as radiometric, enzymatic, fluorescent, colorimetric, can be implemented in alternative embodiments under the present invention as well, whereby each system is configured to interrogate the sample using corresponding physical properties measurable by the particular system.

The illustrated monitoring system 200 can be used to monitor a variety of different bio/chemical activities, such as binding events. In an exemplary embodiment of this application, all or a portion of the surface area of the first and second measurement probes 180 and 190 (and/or corresponding signal grounds 187 and 197) is suitably prepared to induce or inhibit specific binding events. A non-exhaustive list of possible modifications include: modifications designed to induce the specific binding of one or more analytes, such as antibodies specific for a given epitope of an analyte; proteins, nucleic acids, lipids, and/or carbohydrates, which are know to, or suspected of, binding other molecules of interest, such as small organic and inorganic molecules of therapeutic interest, proteins, nucleic acids, lipids, and/or carbohydrates. Other modifications may include: cells, cellular structures such as cell membranes, organelles, surface receptors, and the like, may be attached to the surface of measurement probes 180 and/or 190 (and/or corresponding signal grounds 187 and 197), for the purposes of detecting activities within the said cells and/or structures, optionally in response to one or more properties of the sample which is supplied to the device. Said cells and substructures may be identical (or as close as possible thereto) for the surface area of both measurement probes 180 and 190, or the surface of each measurement probe may one be different. Such differences may include the use of cells with differing genetic and/or phenotypic makeup on the binding surface of measurement probe 180 relative to 190, for the purposes of making comparisons between one cell type and another. In one exemplary embodiment of the invention, a population of reference cells-cells with a specific set of properties, is placed on the surface of the first measurement probe, whereas another population of cells is placed on the surface of the second measurement probe 190, which have one or more known and/or determinable differences which render them capable of at least one specific activity separate, distinct, and unique from the population of cells disposed on the surface of the first measurement probe 180.

The attachment of the previously mentioned structures may be facilitated by the use of any of the well-known techniques for the immobilization of molecules or other structures such as cells, to the surfaces of measurement probes 180 and 190 (and/or corresponding signal grounds 187 and 197), as are known skilled in the art of surface chemistry. A partial list of such techniques is: self-assembled monolayers of alkanethiolates such as $CH_3(CH_2)_N$—SH which are ω-carboxylated for additional attachment of linker chemistries, such as EDC and NHS esters; or hydrophobic monolayers, such as non-carboxylated alkanethiolates, for the non-specific attachment of proteins, cells, and the like.

Alternatively, the surface of measurement probes 180 or 190 (and/or corresponding signal grounds 187 and 197) may be modified in such a manner as to exclude or inhibit any type of binding from the sample or substances contained therein. Such modifications include, but are not limited to: any of the surface chemistries well known in this art, which reduce the binding potential of aqueous-based substances, such as polyethylene glycol (PEG), alkanethiolates such as $CH_3(CH_2)_N$—SH which may be ω-carboxylated for additional attachment of PEG or other linker chemistries useful in the attachment of proteins and other capture chemistries; other chemistries, such as the use of various proteins, such as BSA, which block binding of other proteins and cells. In some embodiments of the invention, several of the above modifications may be made in the same device. One exemplary embodiment employs specific binding chemistries along the surface of the first measurement probe 180 (and/or corresponding signal ground 187), whereas the surface of the second measurement probe 190 (and/or signal ground 197) are modified to exclude any type of binding from substances within the sample.

Once the system is fabricated to include the above-mentioned properties, and is connected to a power source, as well as endowed with a means to capture and store the data, a specific assay is developed as follows: The surface of the first or second measurement probes 180 or 190 is selected as a reference. For example, if one desires to examine a particular sample for the presence of a certain molecular analyte, one optionally chooses the surface of the first measurement probe 180 to be modified such that little measurable binding occurs thereon, whereas surface area along the second measurement probe 190 is modified to include capture chemistries designed to specifically bind said analyte, for example through the use of protein-A as a means to link the population of antibodies to the surface of the gold electrodes.

Next, the system may be calibrated through the use of one or more calibration procedures. For example, a calibration solution, optionally of similar electrical properties as the sample to be examined, is supplied to the device, and the voltage difference at the output of the third differential amplifier 226 is noted, as well as the phase difference as measured by the phase meter 223, if such an instrument is employed. Said calibration may be applied immediately before the subsequent step, may be done at some point earlier, may be done using a computer model or simulation, or may be done using a representative or proxy for the device actually being used. One may optionally include in the calibration process one or more steps which are designed to achieve a better null in the signal, said better null being achieved through the use of variable bias, gain, and/or resistance on one or both of the differential amplifiers 221 and/or 222. Other means may be employed as well to achieve a better null, as is well known to those skilled in the art.

Next, the sample solution, which is suspected of containing an analyte to which the population of immobilized antibodies specifically binds, is supplied to the device. The difference signal 227 (e.g. output voltage) is measured and recorded, optionally along with the measured phase difference by phase meter 223. A change in the difference signal 227 beyond a pre-defined threshold is indicative of the specific analyte-antibody binding. A change in the difference signal 227 below said threshold is indicative of a lack of binding, and therefore that the sample does not contain the specific analyte in question. In addition, the magnitude of the difference signal 227 can be correlated to the amount of binding which has occurred. Further, the rate at which the difference signal changes can be correlated to the binding rate. Similarly, the phase difference measurement may also be used to determine whether binding has occurred, and if so, to what degree. That is, a change in the measured phase difference beyond a pre-defined threshold may be indicative of the specific analyte-antibody binding. A change in the measured phase difference below said threshold accordingly would indicate a lack of binding, and therefore indicates that the sample does not contain the specific analyte in question. When binding is detected, the magnitude of the measured phase difference may optionally be correlated to the amount of binding which has occurred. The monitoring system 200 may be controlled by a microprocessor and/or computer, and the data extracted from the difference meter 240 may be stored, interpreted, displayed and/or acted upon by or through the use of a computer or other digital device.

Figure 2B:
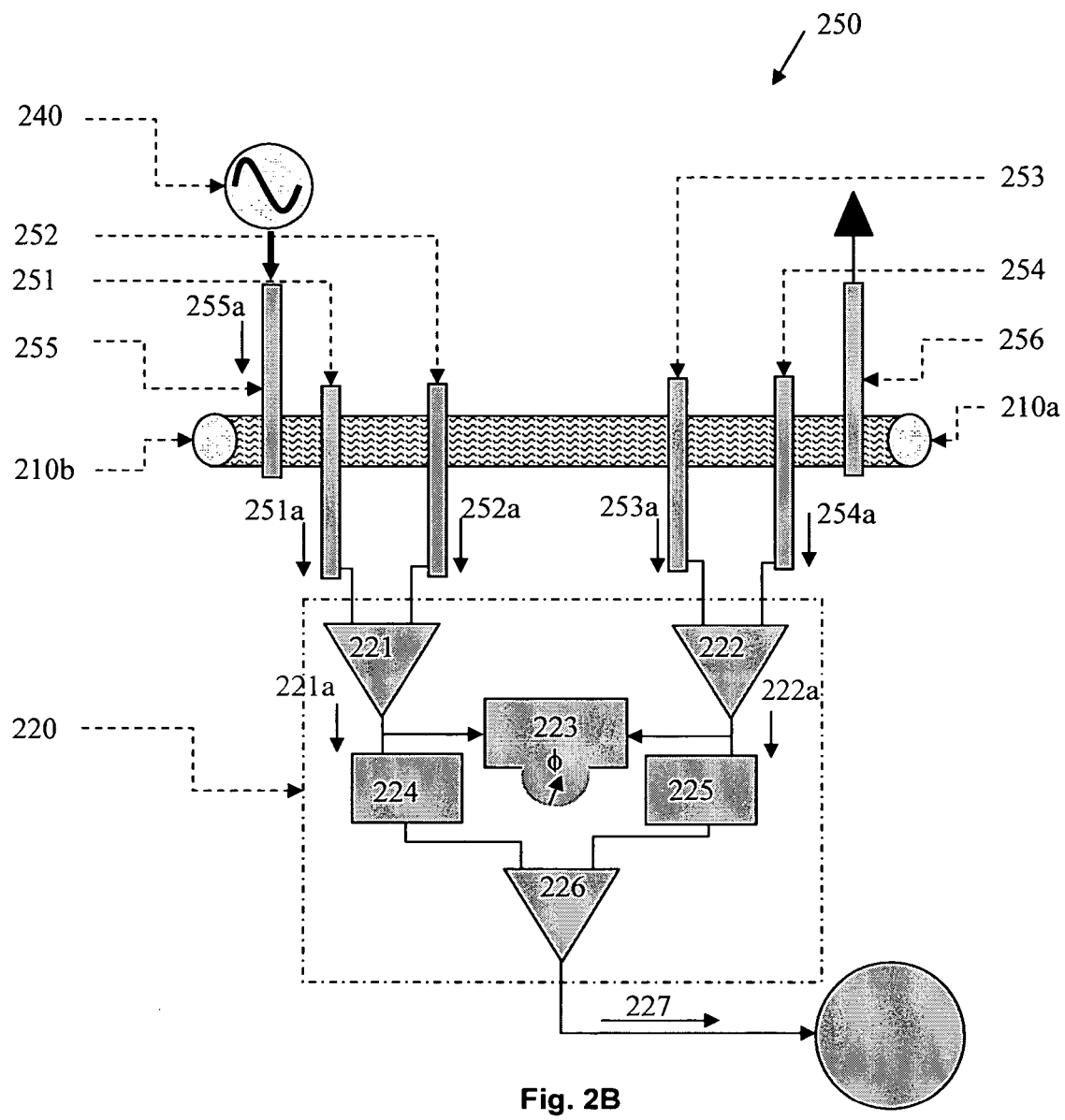
FIG. 2B illustrates a second embodiment of a single sample monitoring system in accordance with the present invention.

FIG. 2B illustrates a second embodiment of a single sample system for monitoring bio/chemical activities in accordance with the present invention, with previously defined components and features retaining their reference numerals. This embodiment is especially useful in obtaining a measurement gradient (e.g., a voltage gradient) between two or more measurement probes coupled to the sample.

In this embodiment, four measurement probes 251, 252, 253 and 254 are coupled to the sample at separate locations. A signal probe 255 and a signal ground probe 256 are also coupled to the sample at separate positions. The signal probe 255 operates to couple a test signal 255a to the sample. The measurement signal couples to the sample, and travels along the length of the sample chamber 210 to the signal ground probe 256 where it returns to ground (ac or dc) potential. The test signal 255a is modulated or otherwise altered by bio/chemical activities occurring within the sample as it moves through the sample. These changes may occur, for example, because of changes in the bulk properties of the solutions at or near each of the probes 251-253. Examples of bulk properties include, but are not limited to: cellular and tissue activities within the sample, such as cell proliferation, migration, and other structural, chemical and morphologic properties. Other bio/chemical activities measurable may be the depletion of a particular analyte in the sample due to an immobilized binding partner at or near one or more of the probes 251-254. Measurement probes 251-254 receive the measurement signal in its condition at the probes' respective locations the measurement probes 251-154 outputting respective measurement signals 251a-254a to the comparator 220.

The comparator 220 includes the previously described first and second differential amplifiers 221 and 222, an optional phase meter 223, optional first and second DC converters 224 and 225, a third differential amplifier 226, and a difference meter 230. However, in comparison to the embodiment shown in FIG. 2A in which one side of both differential amplifiers 221 and 222 are coupled to a signal ground, all inputs of the differential amplifiers 221 and 222 are coupled to one of the four measurement probes 251-254. In the particular embodiment illustrated, the first differential amplifier 221 is coupled to receive as differential signals the first and second measurement signals 251a and 251b, and the second differential amplifier 222 is coupled to receive as differential signals the third and fourth measurement signals 251c and 251d. Accordingly, the first differential amplifier 221 outputs a signal 221a corresponding to the difference in measurement signals 251a and 251b, and likewise the second differential amplifier 222 outputs a signal 222a which corresponds to the difference in measurement signals 251c and 251d. Subsequently, these output signals are in turn supplied to the third differential amplifier 226, which outputs the difference signal 227, the difference signal 227 corresponding to the difference between 221a and 222a, which is the difference between two comparisons of 251a and 252a, and 253a and 254a. The system may further include a correlator (not shown) coupled to receive the difference signal and which stores the characteristics of previously obtained difference signals, each of which has a known bio/chemical activity associated therewith. The characteristics of these stored difference signals (i.e., the difference signal's magnitude, phase, time rate of change, etc.) can then be compared against to the presently measured difference signal to determine bio/chemical activity in the presently measured sample.

In an exemplary operation, a voltage is placed across the sample between the signal probe 255 and the signal ground probe 256, said voltage being of either AC or DC nature, as defined previously. The voltage is applied to the signal probe 255 and is subsequently coupled to the sample as the term "coupled" is defined herein. The voltage migrates through the sample and returns to ground via signal ground probe 256. The voltage drop between measurement probes (e.g., 251 and 252) is measured by those probes output signals (e.g., 251a and 252a). Alternatively, any pair-wise measurement of voltage differences may optionally be measured, irrespective of order or sequence in the sample chamber 210.

Next, the measurement signals 251a-254a are differenced and amplified though the first and second differential amplifiers 221 and 222, as shown, and the relative phases of the two resulting output signals 221a and 222a are compared by phase meter 223 using phase comparison techniques well know to the art. The resulting phase difference is recording using data recoding techniques also well known to the art. If the output signals 221a and 222b are not in DC format, then they may optionally be converted thereto by means of optional DC converters 224 and 225, previously described. In this case, the respective outputs of 210a and 210b are both DC values, and are optionally fed into a second amplification device 220, in such a manner that the voltage comparison is made directly between the out put of 210a and 210b, as illustrated in FIG. 3. Alternatively, the voltage difference between the output of 210a and 210b may be measured and recorded directly, with any of the devices and methods capable of doing so, as are well known in the art. The resultant DC-formatted signals are then supplied to the third difference amplifier 226, which outputs in response, the difference signal 227. The difference signal 227 is input to the difference meter 230 which indicates the relative difference between the output signals 221a and 222a.

As previously described, a change in the difference signal 227 beyond a pre-defined threshold is indicative of the presence of one or more bio/chemical activity(ies). A change in the difference signal 227 below said threshold is indicative of a lack of activities. In addition, the magnitude of the difference signal 227 can be correlated to the amount of activity which has occurred. Further, the rate at which the difference signal changes can be correlated to the rate of activity. Similarly, the phase difference measurement may also be used to determine whether one or more bio/chemical activities have occurred, and if so, to what magnitude and at what rate, if desired.

In another embodiment, one or more reactive centers may optionally be placed in the sample chamber 210, for example one or more biological cells prepared according to the necessities of the experiment, said reactive center designed to cause one or more specific biologic or chemical activities in some volume of the sample chamber (e.g., between two of the measurement probes). A sample is placed in the desired location within the sample chamber 210, the sample known to, or suspected of containing one or more properties which exhibit one or more specific bio/chemical activities. Said activities may occur when placed in proximity to the optional reactive center, or may occur via a stimulus or inhibition via another source, or may occur spontaneously. Alternatively, local differences in the electrical properties of the sample may be measured, said measurement being used for monitoring movement of a sample through the sample chamber 210, diffusion of one or more constituents within the sample chamber 210; for the purpose of monitoring the electromagnetic properties of biological cells, either in response to stimuli or not; or for other uses.

Next, the sample solution is supplied to the device. The difference signal 227 is obtained, optionally along with the phase difference. A change in the difference signal 227 beyond a pre-defined threshold is indicative of change in the bio/chemical activity in the sample. A change in the difference signal below a predefined threshold is indicative of a lack of change. Further, the amount the difference changes may optionally be correlated to the amount of bio/chemical activity which has occurred. Similarly, phase information may be used to detect the presence or absence of the bio/chemical activity within the sample, or the level of activity within the sample as well.

Further alternatively, the surface of one or more of the measurement probes 251-254 may be prepared as described above to have a high or low binding affinity to a particular analyte. The surface of each measurement probed may be prepared to have high or low binding affinity to the same analyte, or alternately, the surface of each probe 251-254 may be prepare to have high or low binding affinity to different analytes.

The system is optionally calibrated through the use of one or more calibration procedures. A calibration solution, for example, of similar electrical properties as the sample to be examined, is supplied to the sample chamber 210, and the difference signal 227 is obtained, as well as the phase difference as measured by the phase meter 223, if such a measurement is employed. Said calibration may be applied immediately before the subsequent step, may be done at some point earlier, may be done using a computer model or simulation, or may be done using a representative or proxy for the device actually being used. One may optionally include in the calibration process one or more steps which are designed to achieve a improved null in the signal, said improved null being achieved through the use of variable bias, gain, or resistance on one or both of the differential amplifiers 221 and/or 222. Other means may be employed as well to achieve a better null, as is well known to those skilled in the art.

Next, the sample solution, which is suspected of containing an analyte to which the reactive center may respond, is supplied to the sample chamber. The difference signal 227 is measured and noted, optionally along with the phase difference. A change in the difference signal 227 beyond a pre-defined threshold is indicative of the activity or activities of the specific analyte. A change in the difference signal 227 below said threshold is indicative of a lack of activity. Further, the magnitude of the voltage change may optionally be correlated to the amount of activity which has occurred. Still further, the time rate of change of the voltage difference may be correlated to the time rate of change or progression of the activity. The phase meter 223 may also be used to detect the presence or absence of activity, and binding rate based upon the amplitude of the measured phase difference and time rate of change thereof. Additional information on the nature and extent of activities may be revealed by the properties of the probe signal, and its modulation due to activities within the sample, said properties of probe signal may include frequency, wavelength, amplitude, duration, and the like. As above, the monitoring system 250 may be controlled by a microprocessor and/or computer, and the data extracted from the difference meter 240 may be stored, interpreted, displayed and/or acted upon by or through the use of a computer or other digital device.

Figure 2C:
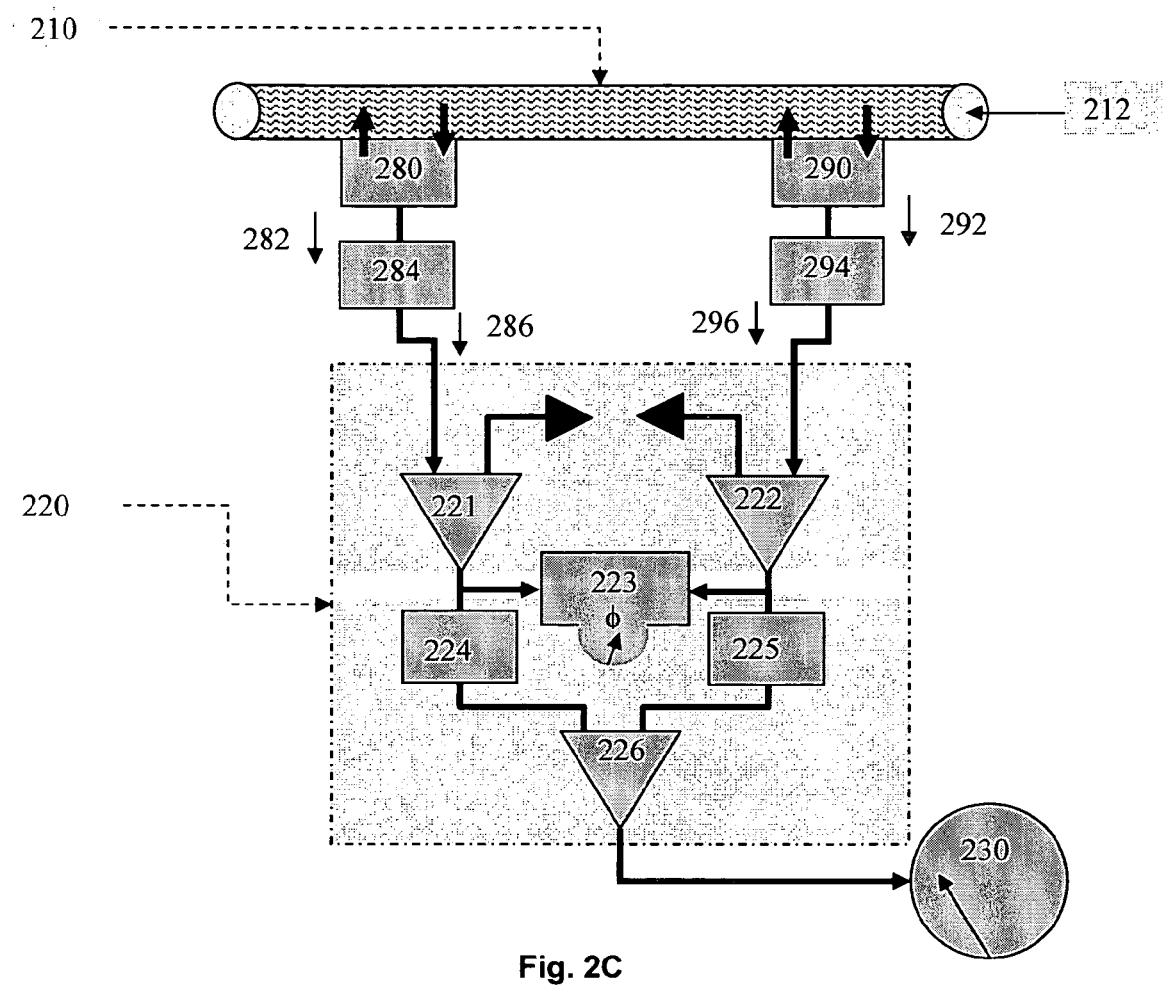
FIG. 2C illustrates a third embodiment of a single sample monitoring system in accordance with the present invention.

FIG. 2C illustrates a third embodiment of a single sample system for monitoring bio/chemical activities in accordance with the present invention, with previously defined components and features retaining their reference numerals. This embodiment describes a monitoring system which employs non-electronic based measurement probes 280 and 290, the outputs of which are non-electronic signals.

In this embodiment, the measurement probes 280 and 290 interrogate the sample 212 and, in response, produce respective measurement signals 282 and 292, which are not electrical/electronically-based. For example, the measurement probe may comprise an optical lens operable to collect light modulated by the sample. The non-electronic measurement signal is subsequently converted to an electronic-based signal by means of respective converters 284 and 294, which in the case of the previous example, would be one or more photodiodes. The converted electronic signals 286 and 296 are then supplied to the comparator 220, which in one embodiment is as previously described in FIG. 2A. Detection of the presence of absence of one or more bio/chemical activities, as well as the magnitude and rate of the activity is as previously described. As described above, the system may further include a correlator (not shown) operable to compare characteristics of stored difference signals against to the presently measured difference signal to determine bio/chemical activity in the presently measured sample.

Multiple Sample Monitoring Systems

Several embodiments of a multiple sample monitoring system are now provided, each system being configurable in either of the differential signal architectures of FIG. 1A or 1B. The multiple sample monitoring system may be preferred over the single sample system in certain applications, for example, to directly compare a test sample which is suspected of containing a particular bio/chemical activity to a reference sample which is known to contain the sought activity. The parallel architecture of the multiple sample system can be expanded, such that any number of samples can be concurrently compared against a test sample, thereby permitting an enhanced high throughput capability for monitoring one or more bio/chemical activities. Examples of applications include, but are not limited to: comparisons between multiple wells in an open-well microtiter plate of bio/chemical activities, such as cell response to stimulus or inhibition, or variation in environmental conditions such as nutrient content, hormones, other physiologic factors, small molecules of synthetic or natural origins; binding of organic and non-organic molecules to specific capture chemistries within one or more of the multiple sample chambers, for the purposes of determining the presence and amount of one or more analytes; comparisons between multiple enclosed fluidic channels for bio/chemical activities, detecting diffusion properties such as cell motility and migration as well as the passive diffusion of molecules within a closed structure; and the like. The reader will appreciate that the multiple sample monitoring system is not limited exclusively to making the aforementioned measurements, and that it may be employed to monitoring any bio/chemical activity.

Figure 3A:
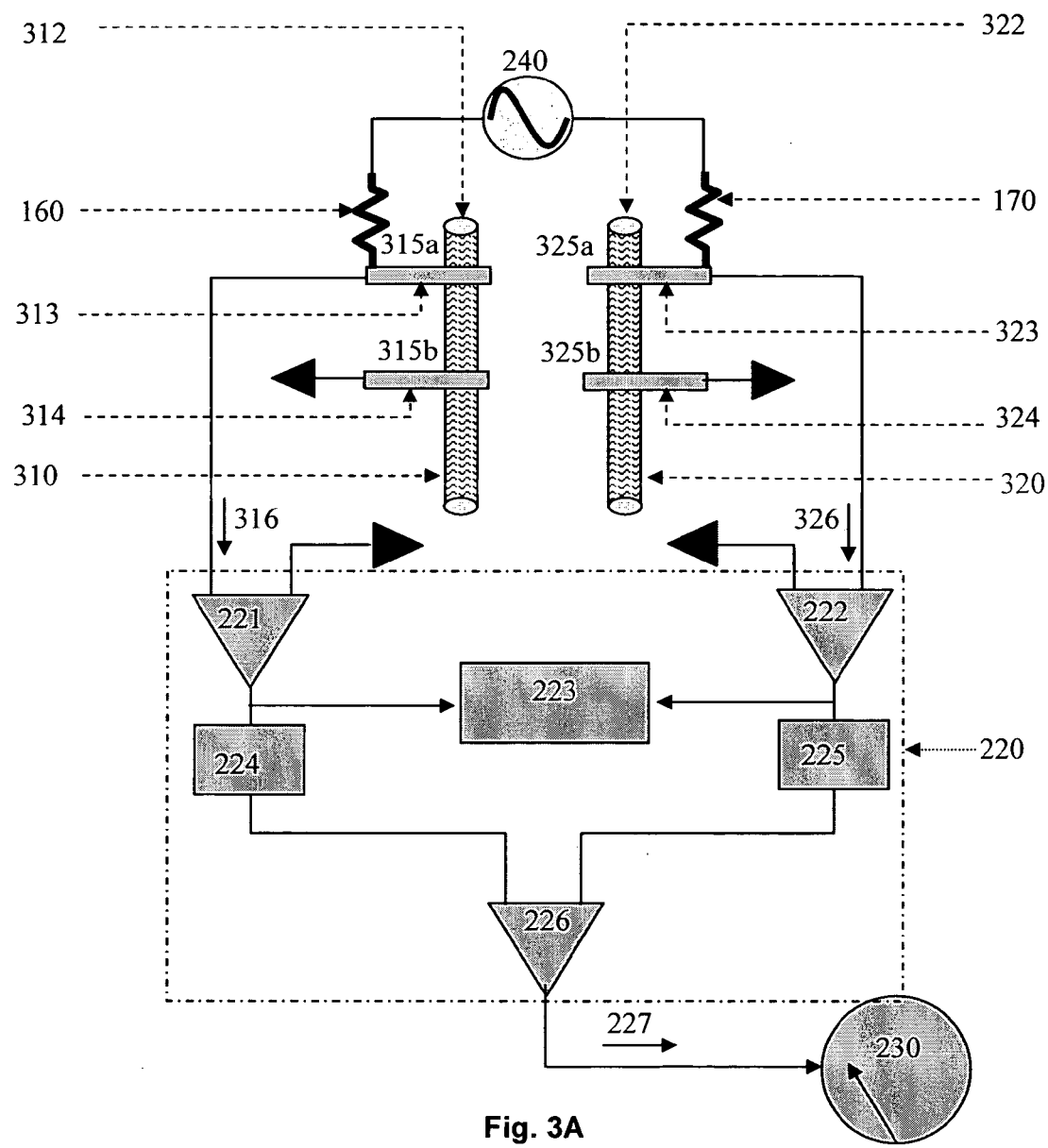
FIG. 3A illustrates a first embodiment of a multiple sample monitoring system in accordance with the present invention.

FIG. 3A shows a first embodiment of a multiple sample monitoring system in accordance with the present invention, with previously identified features retaining their reference numerals. The system includes first and second sample chambers 310 and 320 through which respective first and second samples 312 and 322 flow. The signal source 240 provides test signals 240a and 240b to first and second sample chambers 310 and 320 via reference elements 160 and 170. In an exemplary embodiment shown, reference elements 160 and 170 are resistors of substantially identical value, such that the test signal applied to the first and second measurement probes 313 and 323 is substantially the same. Further, the resistance values may be selected such that one half of the total applied voltage is present on each of the measurement probes 313 and 323.

The test signal is applied to the first sample 312 by means of the first measurement probe 313 which is coupled to the first sample 312 at position 315a. The test signal propagates through the first sample 312, its physical properties (e.g., conductivity) being modulated by the bio/chemical activities occurring therein, the applied test signal returning to ground potential at the signal ground 314 located at 315b. As noted above, the measurement probes and/or corresponding signal grounds may be in direct contact with the respective first and second samples, or alternatively coupled indirectly to the samples by means of an intervening structure (e.g., a electromagnetically or optically transparent material, when the interrogating signal is electromagnetic or optical).

In parallel, a test signal is applied to the second sample 322 at position 325a. This test signal propagates through the second sample 322, its conductivity, impedance, or other physical properties being modulated by the bio/chemical activities occurring within the second sample, the second applied test signal returning to ground via a signal ground 324 located at 325b. In the exemplary embodiment shown, the values of the two resistors 160 and 170, the dimensions of the sample chambers 310 and 320, and the construction of the measurement probes 313 and 323, corresponding signal grounds 314 and 324, and spacing therebetween are substantially identical, so that any difference between the two measurement signals 316 and 326 is attributable to a difference in the bio/chemical activities occurring within the first and second samples 310 and 320, including activities occurring on or near the surface of one or more of the measurement probes 315a-b and 325a-b.

The monitoring process can be performed in substantially a similar manner as described above, with the additional feature that bio/chemical activities occurring within different first and second samples 312 and 322 maybe directly compared. For example, the first sample 312 may be used as a reference, against which a sample 322 may be compared. As an example, the first and second measurement probes are prepared to induce binding to a particular binding partner. Next, a reference sample known to contain the binding partner is supplied to the first sample chamber, and a test sample suspected of containing the binding partner is supplied to the second sample chamber. A measurement is performed and when the resultant difference signal 227 is within a predefined range, the test sample is determined as having the particular binding partner. Alternatively, the first and second measurement probes (for example 315a and 325a) may be prepared to induce binding to a particular analyte, whereas the other two measurement probes (for example 315b and 325b) are prepared such that the analyte does not bind. A sample suspected of containing the specific analyte is then placed in both chambers 310 and 320. A resulting change in the difference signal 227 above a pre-defined threshold is indicative of binding between the specific analyte and the prepared surface(s) of 315a and/or 325a. The embodiment may be expanded to include a third, fourth or additional sample chambers to compare a plurality of unknown samples against the reference. As described previously, the system may further include a correlator operable to compare characteristics of stored difference signals against to the presently measured difference signal to determine bio/chemical activity in the presently measured sample.

Figure 3B:
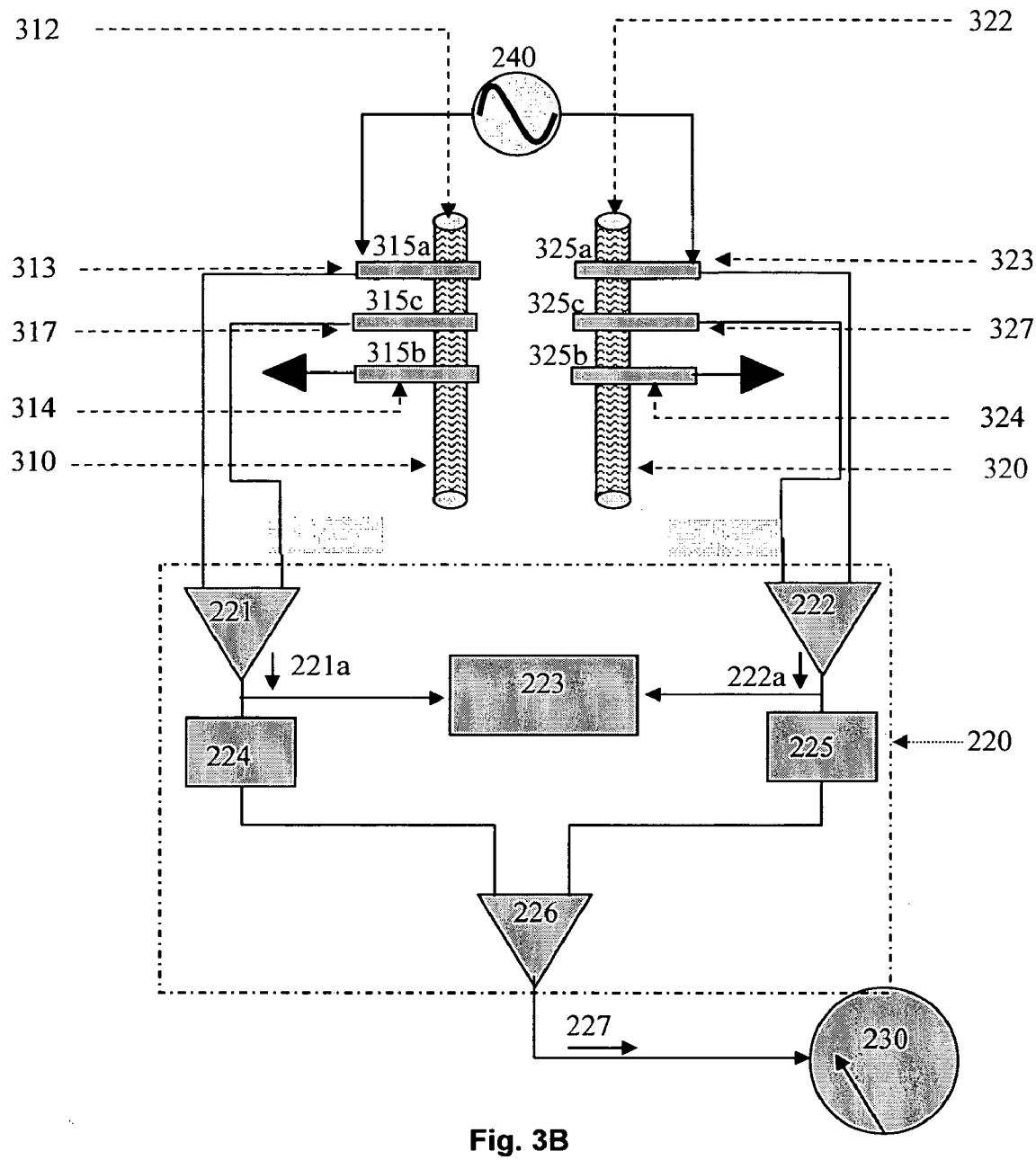
FIG. 3B illustrates a second embodiment of a multiple sample monitoring system in accordance with the present invention.

FIG. 3B illustrates a second embodiment of a multiple sample monitoring system in accordance with the present invention, with previously identified features and components retaining their reference numerals. This embodiment is similar to that shown in FIG. 2B in which a measurement gradient (such as voltage gradient) can be obtained.

In this embodiment, first sample measurement probes 313 and 317 are coupled to the first sample 310 at locations 315a and 315c, and second sample measurement probes 323 and 327 are coupled to the second sample 320 at locations 325*a* and 325*c*. A first signal ground 314 is coupled to the first sample 310 at location 315*b*, and a second signal ground is 324 is coupled to the second sample 320 at location 325*b*. The signal source 240 couples a test signal directly to the first and second samples 310 and 320 via first and second measurement probes 313 and 323. As shown above, the first and second sample chambers 310 and 320, measurement probes and signal grounds may be constructed so as to be substantially identical, so that direct relative measurements between the two systems can be obtained.

During testing, an applied test signal is coupled to the first test sample 312 and travels from measurement probe 313 to measurement probe 317, returning to ground potential at signal ground 314. Measurement probes 313 and 316 measure physical properties of the sample (e.g., conductivity, impedance, optical absorption and emission, mass and mass/charge ratio properties, wavelength, etc.), and output measurement signals 313*a* and 317*a* to antipodal inputs of the first differential amplifier 221, the difference in these measurement signals corresponding to the difference in bio/chemical activities occurring within the first sample 312. In parallel, the test signal is coupled to the second sample and travels from measurement probe 323 to probe 327, and returns to ground potential at signal ground 324. Measurement probes 323 and 327 measure physical properties of the second sample, and output corresponding measurement signals 323*a* and 327*a* to antipodal inputs of the second differential amplifier, the difference in these measurement signals corresponding to the difference in the bio/chemical activities occurring within the second sample. In this manner, the system of FIG. 3B can be used to monitor differences in bio/chemical activity occurring within a single sample, or between two samples. In particular embodiment shown, the difference signal 227 will indicate the relative difference between two difference measurements, i.e., the relative difference in bio/chemical activity occurring between 315*a* and 315*b* in the first sample, compared to 325*a* and 325*b* in the second sample. These differences may be brought about by, for example, preparing the contents of one channel to include a reference population of biologic cells or tissues, and the contents of a second channel to include a population of cells which are exposed to one or more agents known or suspected of causing bio/chemical activity within said cell population. Other examples include the use of specific capture chemistries preferentially located within one or more channels, such that the binding of one or more analytes specific for the prepared capture chemistry results in a reduction of the analyte in solution as compared to a reference channel, thus effecting a measurable change in a physical property of the solution. Further, the surface of the measurement probe/signal ground as well as other system parameters may be optimized for highest measurement sensitivity. A partial list of means to optimize the system for sensitivity and specificity include: varying the frequency of the applied signal, shortening or lengthening the fluid path between the electrodes, using specific surface chemistries which render the surface able to capture more analyte, or otherwise place more analyte in proximity to the electrode in such a way as to cause the greatest change in one or more electrical circuit parameters of the region near the electrodes. As described above, the system may further include a correlator (not shown) operable to compare characteristics of stored difference signals against to the presently measured difference signal to determine bio/chemical activity in the presently measured sample.

Figure 3C:
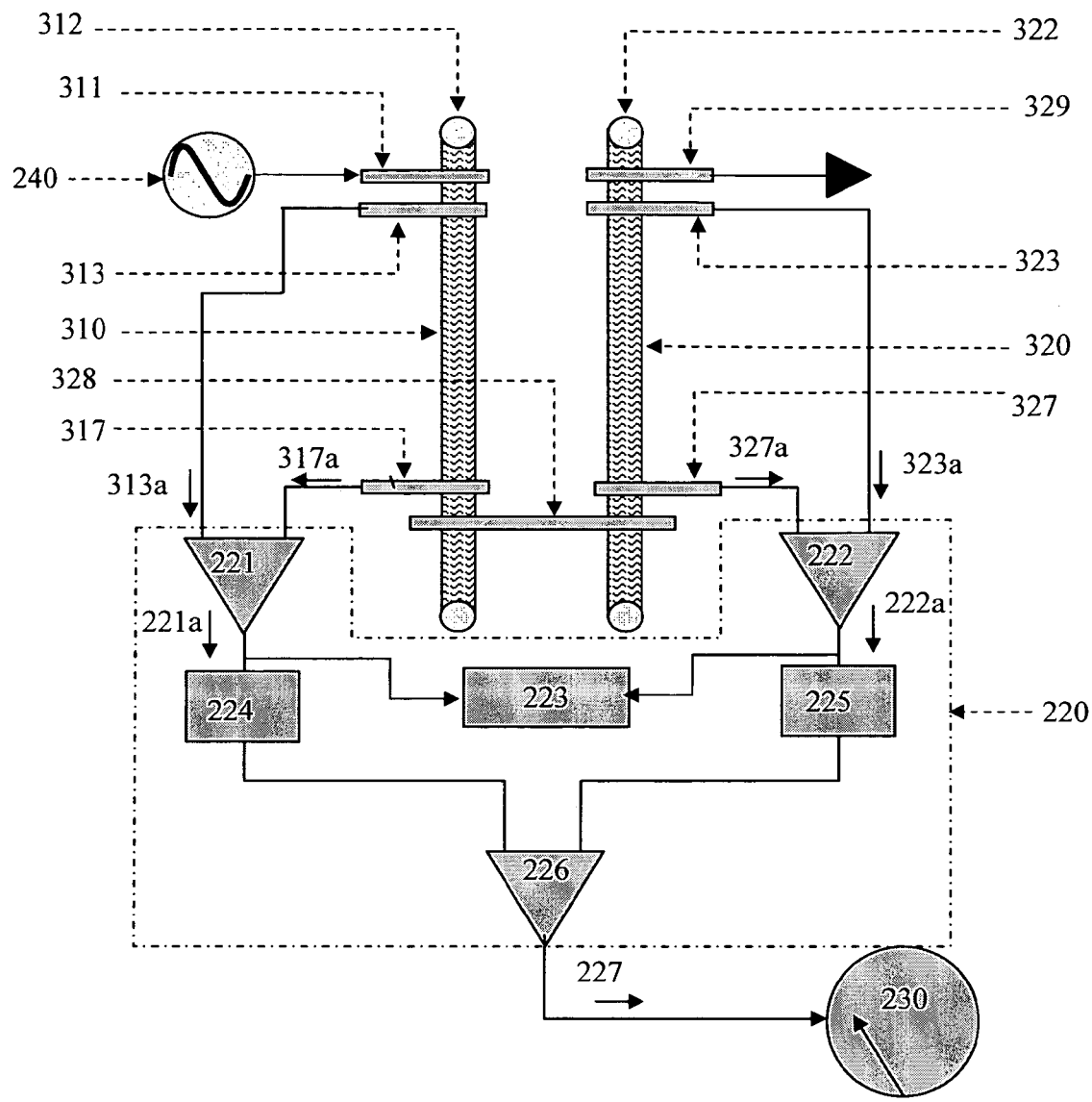
FIG. 3C illustrates a third embodiment of a multiple sample monitoring system in accordance with the present invention.

FIG. 3C illustrates a third embodiment of a multiple sample monitoring system in accordance with the present invention, with previously identified features and components retaining their reference numerals. This embodiment employs a signal probe 311 coupled to the first sample 312, a signal ground 329 coupled to the second sample 322, and a signal path 328 coupled between the first and second samples and operable to support the propagation of a test signal therealong.

In this embodiment, two sample chambers 310 and 320, not in direct fluid communication, are provided, which are designed to hold samples 312 and 322. Also provided are the aforementioned measurement probes 313, 317, 323 and 327, optionally fabricated out of gold or platinum, and optionally fabricated using techniques such as lithography, other techniques as are known in the art, or using methods described herein. A test signal is applied to signal probe 311, the test signal being subsequently being coupled to the first sample 312 by the signal probe. The test signal propagates through the first sample 312, across the signal path 328, through the second sample 322, returning to ground via the signal ground 329, along the way being modulated by bio/chemical activities occurring within the samples. Measurement probe 313, 317, 323 and 327 recover the modulated test signal at different location within the first and second samples, as shown, and producing measurement signals 313*a*, 317*a*, 323*a* and 327 which are supplied to oppositely polarized inputs of differential amplifiers 221 and 222. Output signals 221*a* and 222*a*, and the difference signal 227 are obtained as described above, and the system may optionally employ a correlator as describe above.

Figure 3D:
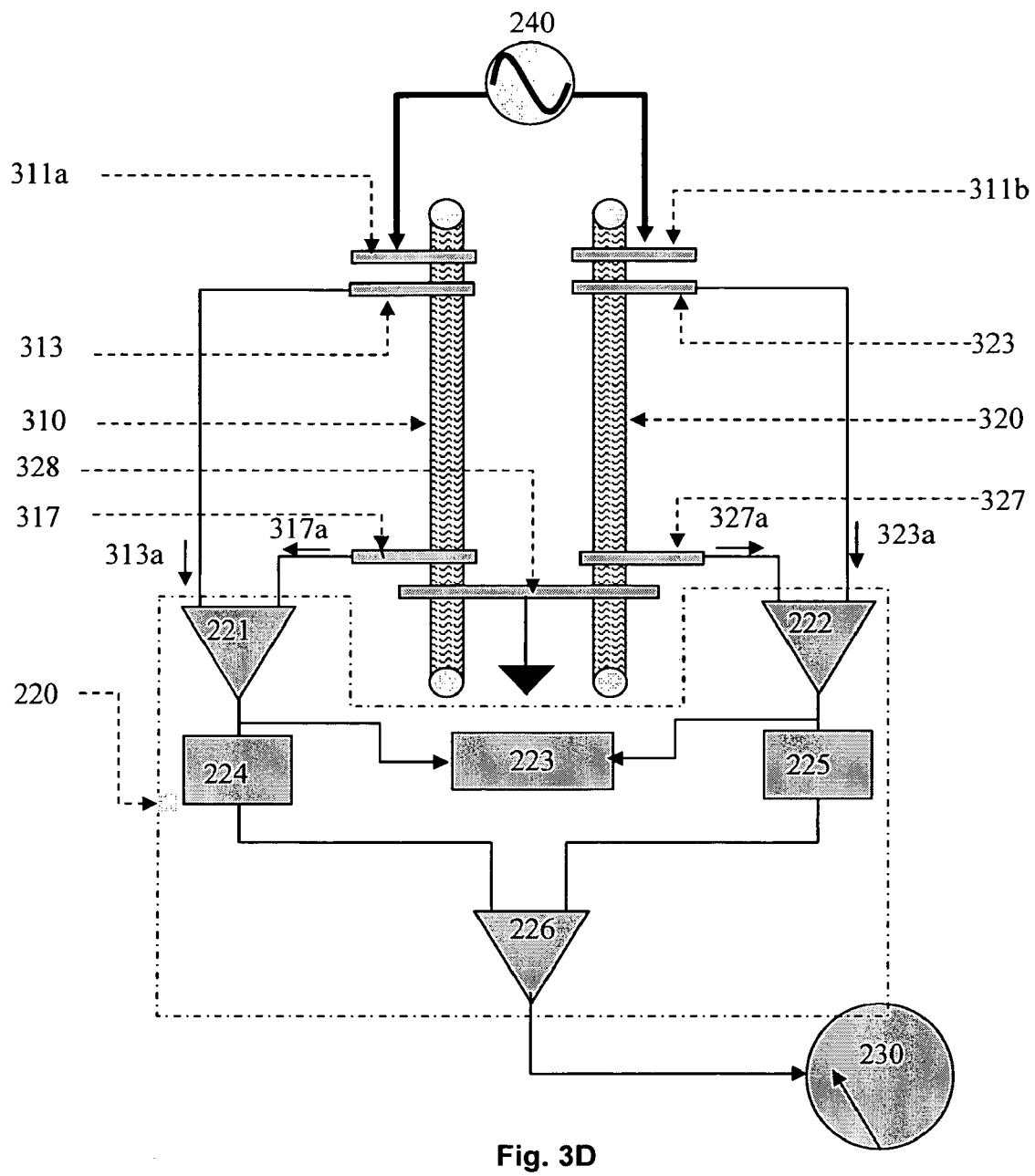
FIG. 3D illustrates a fourth embodiment of a multiple sample monitoring system in accordance with the present invention.

FIG. 3D illustrates a fourth embodiment of a multiple sample monitoring system in accordance with the present invention, with previously identified features retaining their reference numerals. In this embodiment, two signal probes 311*a* and 311*b* are used to apply a test signal to the first and second samples. Signal ground is provided by the previously described signal path 328 which is connected to a signal ground potential. The applied test signal propagates through both samples until reaching the signal path 328 extending between the first and second sample chambers 310 and 320. Measurement probes 313 and 317 output measurement signals 313*a* and 317*a* to detect relative changes occurring in the first sample chamber between those probe locations, and similarly probes 323 and 327 output measurement signals 323*a* and 327*a* to detect changes occurring in the second sample chamber. These relative changes can be further compared against each other by obtaining the difference signal 227, which may be compared against previously obtain difference signals using a correlator as described above.

Figure 3E:
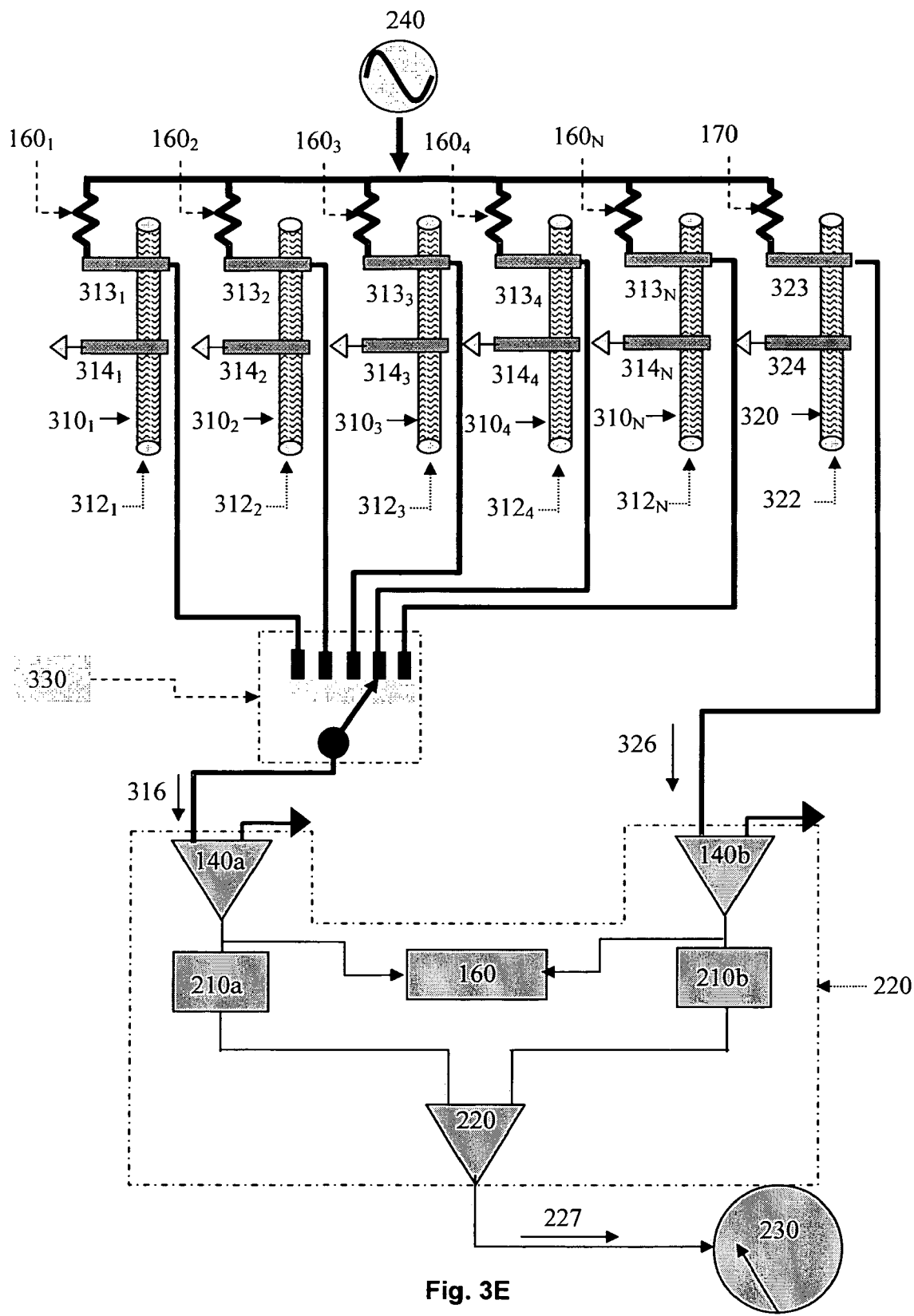
FIG. 3E illustrates a fifth embodiment of a multiple sample monitoring system in accordance with the present invention.

FIG. 3E illustrates a fifth embodiment of a multiple sample monitoring system in accordance with the present invention, with previously-identified features retaining their reference numerals. This embodiment represents an extension to that shown in FIG. 3A, in which a measurement signal from one or N measurement probes is selected for comparison. Particularly, an N×1 switch 330 is operable to select one output signal from any of the N first measurement probes $313_{1-N}$, that measurement signal 316 being routed to the input of the first differential amplifier 221. The second measurement probe 323 provides a measurement signal 326 to the second differential amplifier 222 provides a measure of the difference occurring within the selected first sample $312_{1-N}$ and the second sample 322. In this manner, any of N different samples may be selected to compare against a particular sample.

Figure 3F:
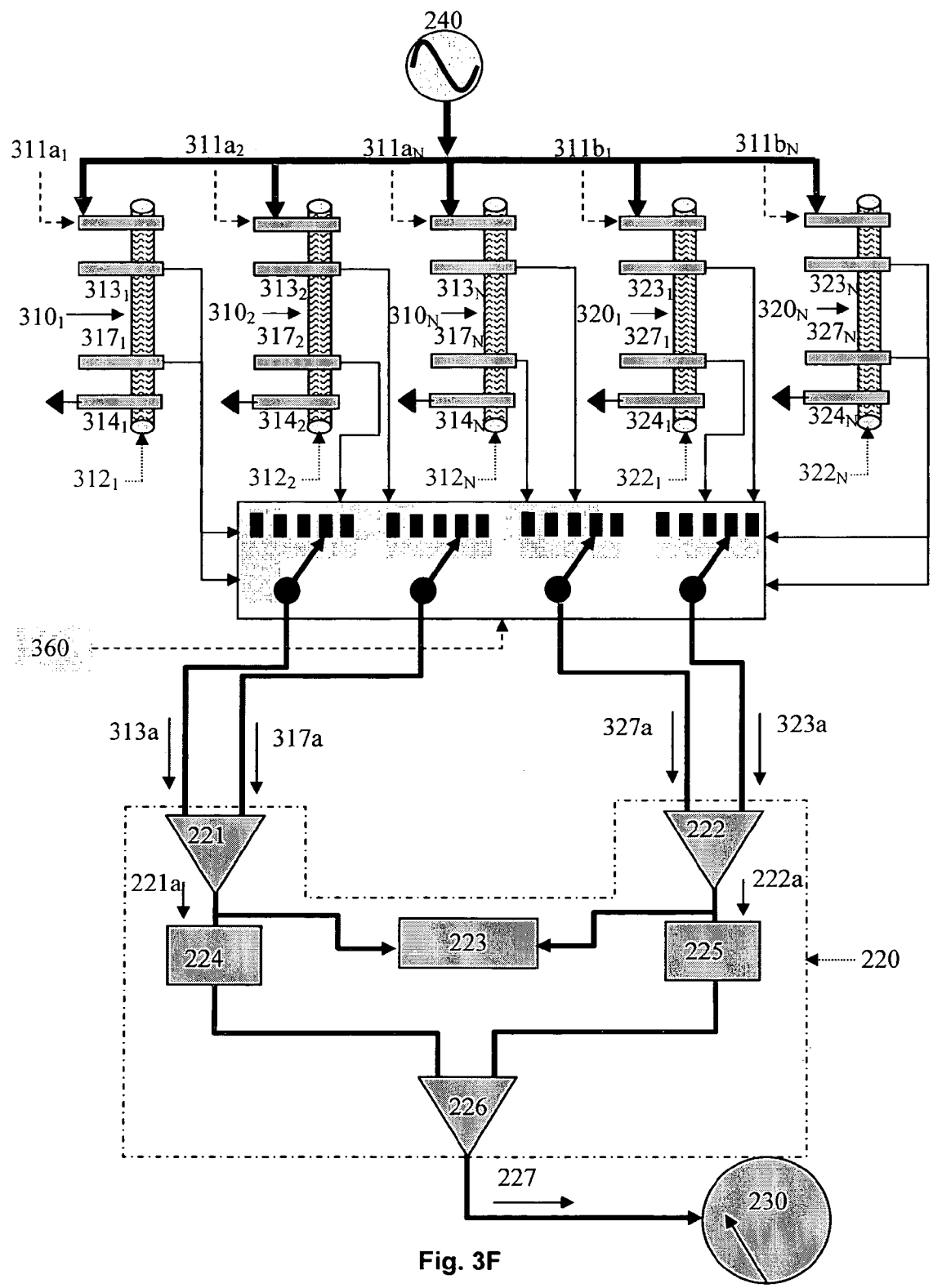
FIG. 3F illustrates a sixth embodiment of a multiple sample monitoring system in accordance with the present invention.

FIG. 3F illustrates a sixth embodiment of a multiple sample monitoring system in accordance with the present invention, with previously-identified features retaining their reference numerals. This embodiment represents an extension to that shown in FIG. 3D, in which the measurement signals of four measurement probes are selected from N different first and second sample chambers $310_{1-N}$ and $320_{1-N}$. Particularly, an N×4 switch 360 is operable to select four output measurement signals 313a, 317a, 323a and 327a from any of the N first and second measurement probes. Each of the four measurement signals is supplied to inputs of the first and second differential amplifiers 221 and 222 as previously described. Output signals 221a and 222a are generated between adjacently selected measurement signals (i.e., 313a and 317a, 323a and 327a), and the difference signal 227 provides a measure of the difference between the output signals 221a and 222a. In this manner, any combination of N different samples may be selectively compared. Further, a correlator (not shown) may be additionally used to compare one or more of the presently measured difference signals against previously obtained difference signals as described above.

Figure 3G:
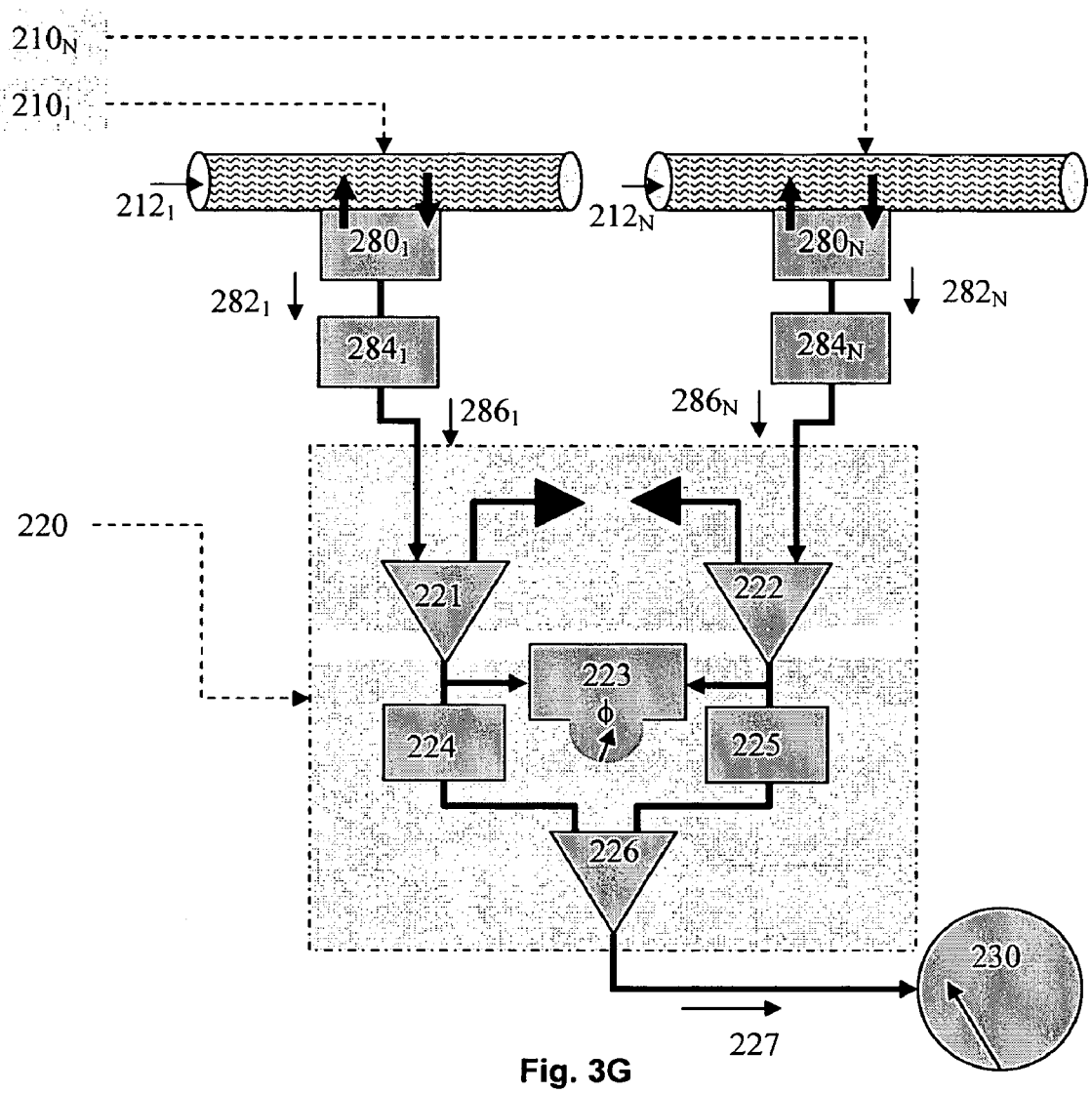
FIG. 3G illustrates a seventh embodiment of a multiple sample monitoring system in accordance with the present invention.

FIG. 3G illustrates a seventh embodiment of a multiple sample monitoring system in accordance with the present invention, with previously identified features retaining their reference numerals. This embodiment represents an extension of that shown in FIG. 2C, in which samples $212_{1-N}$ within N different sample chambers $210_{1-N}$ are analyzed. Measurement probes 2801-N output non-electrical/electronic based signals, each of which are converted to electrical signals, and in one embodiment DC-formatted signals for input to first and second differential amplifiers as shown. In this manner, N different samples may be analyzed using measurement probes which produce non-electrical/electronic (e.g., optical, radiometric, etc.) output signals.

The above descriptions detail certain particular embodiments of the invention described herein. Those skilled in the art of electronics and other areas of detection as covered in the general scope of this application will appreciate that many other electronic configurations may also be employed, and many other chemical and biological systems may be studied, whilst staying within the bounds of the present invention.

Examples

Figure 4:
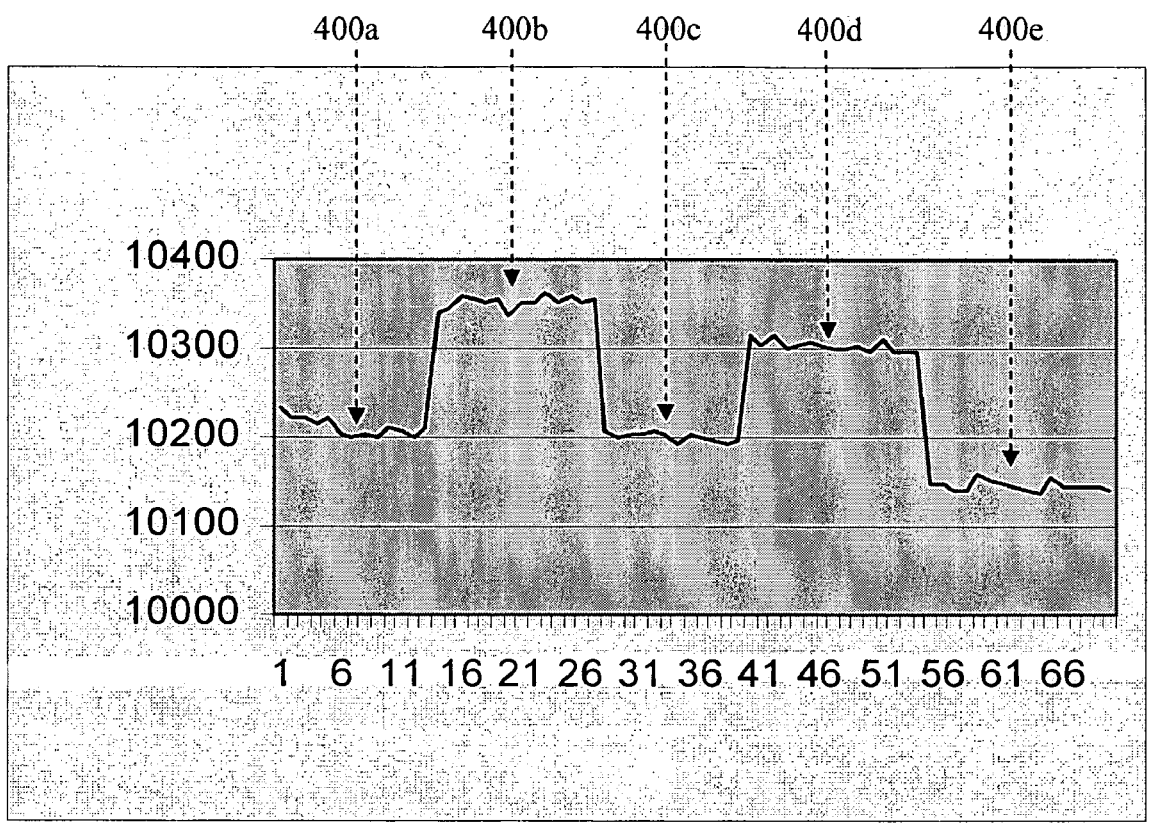
FIG. 4 illustrates the sensitivity of one embodiment of the bridge circuit shown in FIG. 1B.

FIG. 4 shows the basic sensitivity of one embodiment of the bridge circuit described in FIG. 1B, where the comparator 220 (excluding the phase meter 223) as described previously is used to detect small differences in the values of a set of resistors configured as shown in FIG. 1B. A set of four resistors is used, representing 160, 170, 180, and 190 in FIG. 1B, of approximate value of 1000 ohms each. The voltage is measured between 165a and 165b, using comparator 220 as described earlier, and is identified in region 400a in FIG. 4. A second resistor of approximate value 10M ohms (10 million ohms) is then placed in parallel with 160. The resulting change in voltage is identified as the first plateau 400b. This resistor is removed, and the voltage returns to its previous value, shown in FIG. 4 as 400c. This process is repeated in FIG. 4, and is identified by 400d and 400e. This experiment demonstrates the basic sensitivity of the comparator 220, along with the bridge circuit configuration.

Molecular Binding

Figure 5:
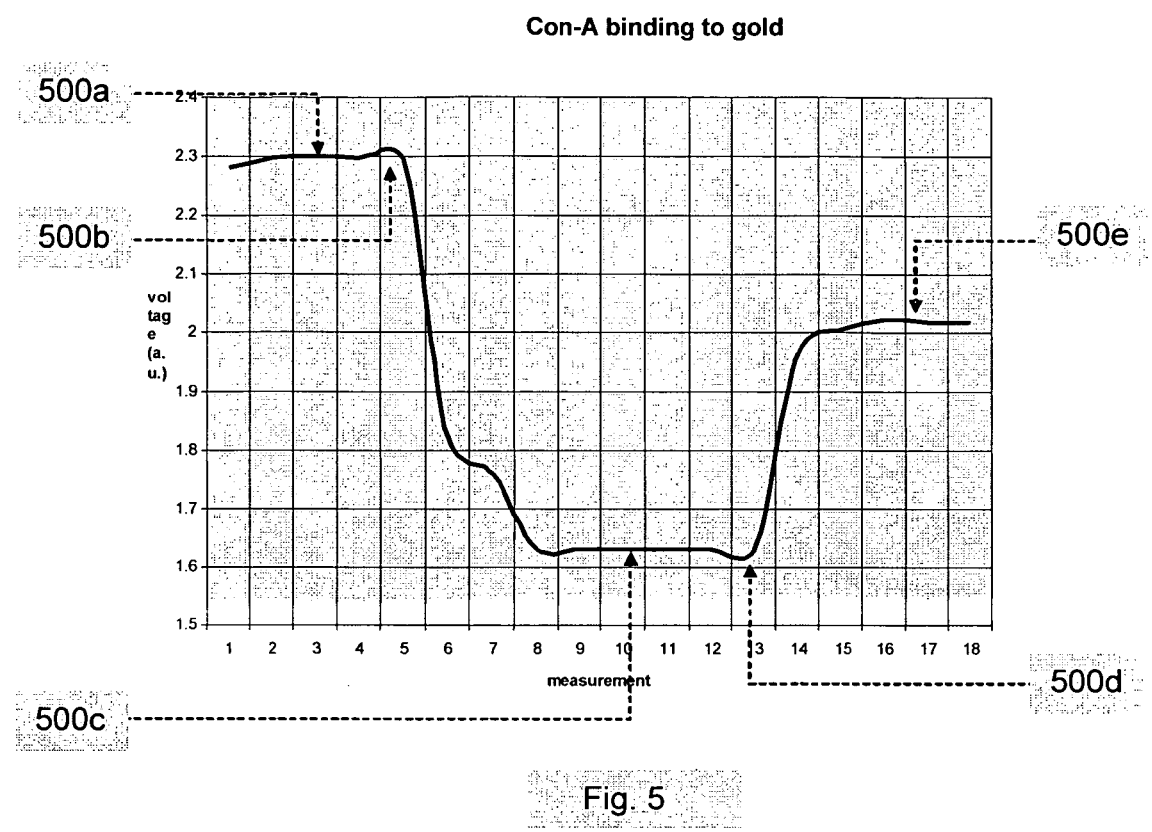
FIG. 5 shows the results of a first experiment using the monitoring system shown in FIG. 3B.

FIG. 5 shows the results of a first experiment using the monitoring system shown in FIG. 3B. A common AC voltage of approximately 40 millivolts and at a frequency of approximately 1 KHz is placed upon measurement probes 313 and 323. The circuit continues across the interface of measurement probes 313 and 323, through the conductive solution in sample chambers 310 and 320, and completed via attachment of signal grounds 314 and 324.

The voltage difference between measurement probes 313 and 317 is placed across the antipodal inputs of the first differential amplifier 221; similarly, the voltage across measurement probes 323 and 327 is placed across antipodal inputs of the second differential amplifier 222. The amplified differential voltages produced by 221 and 222 are fed into DC-converters 224 and 225 (e.g., root-mean-square averaging devices. The outputs 221a and 222a, being now of a DC nature, are input into antipodal inputs of the third differential amplifier 226, the resulting difference signal 227 being measured by a simple voltmeter 400, said voltmeter referenced to the common ground. This voltage is directly proportional to the difference in the voltage drops across the two pairs of measurement probes 313 and 317, and 323 and 327.

A solution of phosphate buffered saline (with calcium and magnesium) at normal physiologic pH and osmolarity is initially placed in sample chambers 310 and 320, said solutions being of nearly identical conductivity, and without additional constituents capable of significantly irreversible binding to any of the electrodes in fluid communication with said solution. The difference signal 227 is measured over a number of measurement points, and is represented by region 500a in FIG. 5. A second solution of an identical buffer, but now containing the additional element in the form of the protein concanavalin-A, is used to replace the solution in the first sample chamber 310, and the voltage is shown as region 500b in FIG. 5. The buffer with the protein is allowed to sit in the channel until equilibrium is reach, as evidenced by the stable voltage reading in region 500c of FIG. 5. Subsequently, the original buffer is used to replace the buffer with the protein contained therein, with the resulting voltage shown in region 500d of FIG. 5. This is followed by numerous exchanges of the contents of the first sample chamber 310 by the original buffer, until equilibrium is reached, as evidenced by the stable voltage in region 500e of FIG. 5. In this state, the voltage represents the residual amount of protein bound to the measurement probes in the first sample chamber 310, as compared to the measurement probes in the second sample chamber 320, which were not exposed to the solution containing the protein.

The overall property demonstrated in FIG. 5 is the capability to detect binding of an analyte to the interface of the electrode and the solution, along with the time rate of change of said binding event. In addition, shifts in the equilibrium of binding are also demonstrated in the transition from region 500c to 500e (through 500d), since the solution in the first sample chamber 310 of FIG. 3B went from favoring the binding of the protein at 500c to favoring the dissociation of the protein at 500d and 500e, on FIG. 5. Since some residual protein remains on the surface of the measurement probe, due to binding of sufficient energy as to make dissociation occur very slowly, the shift in the measured voltage does not return to the initial values in region 500a of FIG. 5, but changes to a new value 500e representing the amount of protein remaining on the measurement probe csurface.

Figure 6:
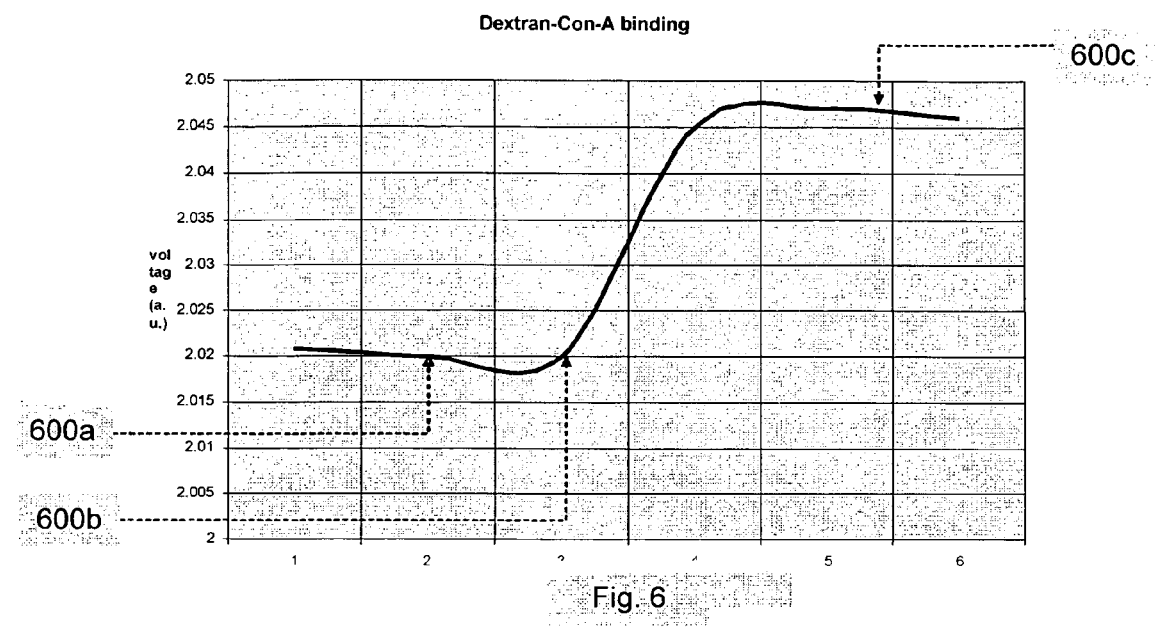
FIG. 6 illustrates the results of a second experiment using the monitoring system shown in FIG. 3B.

FIG. 6 illustrates the result of a second experiment using the monitoring system of FIG. 3B. In this second experiment, a second molecular species in solution is bound to a first molecular species immobilized on the measurement probes in the first sample chamber 310 of FIG. 3B. The first molecular species is concanavalin-A, a protein which specifically binds glucose molecules, as well as polymers of glucose. The second molecular species is dextran, a long-chain polymer of glucose, capable of strongly binding concanavalin-A, immobilized on the surface. The experimental apparatus is identical to the one previously described in the last section, and illustrated in FIG. 3B.

Identical solutions are added to first and second sample chambers 310 and 320 in FIG. 3B, said solutions comprised of phosphate buffered saline with calcium and magnesium, at physiologic pH and osmolarity. The voltage is shown as 600a of FIG. 6. A second solution, identical to the first solution, except for containing a concentration of dextran, is added to the first sample chamber 310 in FIG. 3B, and the change is shown as 600b and 600c in FIG. 6. A new equilibrium is achieved at the solution-electrode interface, comprised of dextran molecules bound specifically to the immobilized concanavalin-A molecules. This new equilibrium is manifest as a new voltage level, as shown in regions 600b and 600c in FIG. 6.

Cellular Activities

The invention described herein can be used to monitor the activities of one or more biological cells, without the need for incorporation of labels or reporter constructs into the cell. This capability results from one or more measurable physiologic changes which occur within cells when their activities are modified. It is not necessary to know beforehand which physiologic changes will occur in a cell, as a result of said modification, nor which subset of said physiologic changes may be detectable. Rather, this embodiment of the invention is useful for the detection of a wide range of activities, the nature of any one of which may or may not be interesting. Stated differently but equivalently, it is useful to know that some cellular response has occurred or has not occurred as a result of one or more modifications of the cell and its environment. Examples of said environmental modification include, but are not limited to: addition of one or more molecular species or structures in the extracellular environment, wherein said molecular species is known to, or suspected of, altering one or more physiologic properties of the cell, said physiologic properties including, but not limited to, biochemical and/or signal pathway or pathways, metabolic activities, morphology, motility, cellular structure such as membrane or internal structure, and the like; interactions with one or more cells in a population, changes in the nutrient conditions of the growth media, addition of biologic molecules such as chemokines, cytokines, and other naturally occurring species—and species derivative thereof—such as secreted proteins and factors produced with cells, and the like.

Figure 7:
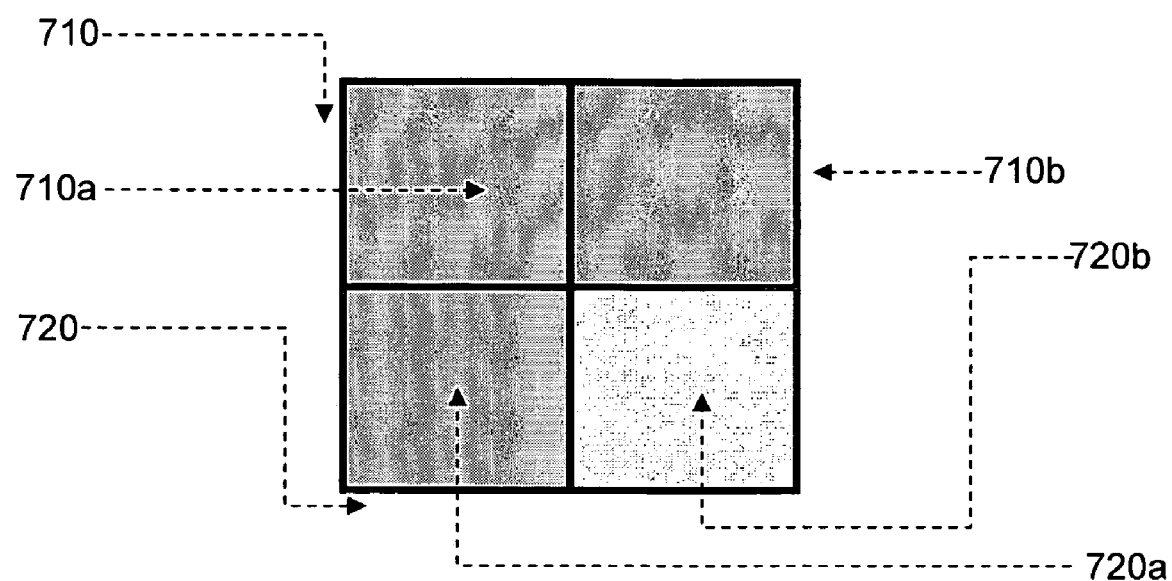
FIG. 7 illustrates a two-by-two experimental matrix for monitoring the signaling pathways of two cell populations.

When the specificity of a given response is desired to be known, a suitable set of cellular properties and/or environmental properties may be prepared such that a set of measured responses corresponding to said cellular and/or said environmental properties will reveal one or more specific activities desired to be detected. For example, one may prepare two populations of cells, one of which has a specific signaling pathway present and/or active within that population of cells; and one population of cells which does not have said signaling pathway present and/or active, which may be accomplished for example by choosing cells with differing genetic make-ups. From these two populations of cells, one then develops a two-by-two experimental matrix shown in FIG. 7, wherein said matrix includes an entry 710a for the cell population wherein said pathway is not active, and an entry 720b for the cell population wherein said pathway is active. The matrix also includes an entry 720a for the cell population with said pathway active, residing in an environment which contains a substance known to inhibit the activity of said pathway, wherein said substance is present in amounts which maximally inhibit the activity of said pathway; and an entry 710b for the cell population which does not have said pathway active, and in which said inhibitor is not present. These four populations of cells are then placed separately in an apparatus which is capable of detecting at least one physiologic change resulting from the modification of said pathway. The cell populations are maintained in environments which support viability and relevant functioning of the cell or cell populations. Next, a substance whose activity against said pathway is desired to be known, is placed in the environment of each of the four populations, in such quantity and proximity as to facilitate any inherent functionality of said substance, in the event that said substance does have one or more activity(ies) against said pathway. The response of the apparatus to each of the four separate populations is noted, and a response above a pre-defined threshold corresponding to the population corresponding to matrix entry 720b in FIG. 7, along with a response below a predefined threshold in the populations represented by entries 710a, 710b, and 720a, indicates that said substance has one or more activities against said pathway. Conversely, the absence of a response as described previously indicates that said substance lacks activity against said pathway. A response in cell populations represented by two or more entries in the matrix indicate that said substance is active against at least one activity of the cell populations, but is not specifically active against said pathway.

One will appreciate that the above example can be generalized and expanded to include more complex test matrices, which represent a plurality of cell populations existing in a plurality of environments. Using apparatuses described herein, one can independently measure the activity of a given cell or cell population in a given environment, against some modification as described previously; the collective set of activity measurements across a pre-defined and pre-characterized set of cells for each modification represents an activity profile for the set of modifications studied.

Figure 8:
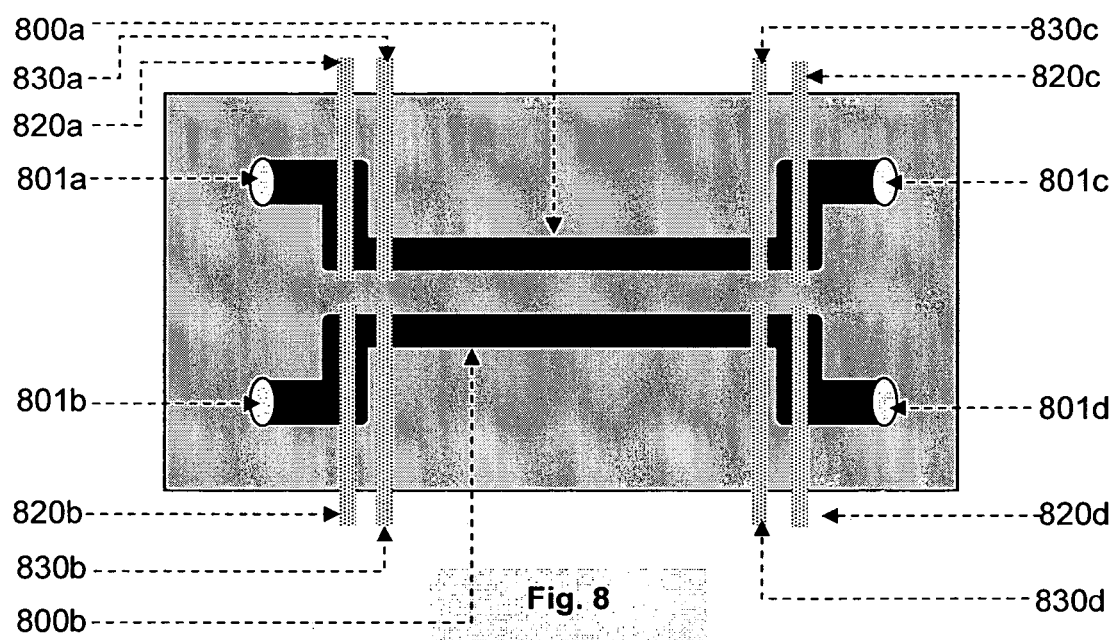
FIG. 8 illustrates a monitoring system used to compare the activity of a known modification of extra-cellular environment to controls.

In this set of experiments, the monitoring system as shown in FIG. 8 was used to directly compare the activity of a known modification of the extra-cellular environment to controls. In the monitoring system of FIG. 8, two sample chambers (formed a fluid channels) 800a and 800b, along with four ports 801a-d, were fabricated using micromachining techniques on an acrylic substrate. The dimensions of the channels were approximately 250 micrometers wide, 100 micrometers deep, and with a total length of approximately 1.5 centimeters. The substrate was fastened in a water-tight manner, using thin film epoxy, to a pre-fabricated printed circuit board (not explicitly shown), on which eight gold-plated copper conductive traces 820a-d and 830a-d of width approximately 250 micrometers were deposited. Using the monitoring system architecture shown in FIG. 3D, in which the phase meter 223 was not present and DC-converters 224 and 225 comprised a device which converts and AC signal into a DC signal, whose amplitude is roughly the root-mean-square (RMS) of the AC amplitude. Antipodal inputs of the first differential amplifier 221 (an operational amplifier) were connected to 830b and 830d, (analogous to measurement probes 313 and 317 in FIG. 3D), and the antipodal inputs of the second differential amplifier 222 (an operational amplifier) were connected to 830a and 830c, (analogous to measurement probes 323 and 327 in FIG. 3D). A common AC signal was then placed across 820a and 820b, which returned to a common ground via 820c and 820d. The difference signal 227 in the monitoring system shown in FIG. 3D was input to a microprocessor capable of storing the output values. Fluid samples were introduced into channels 800a and 800b, via ports 801a and 801b, and extracted via ports 801c and 801d

Figure 9A:
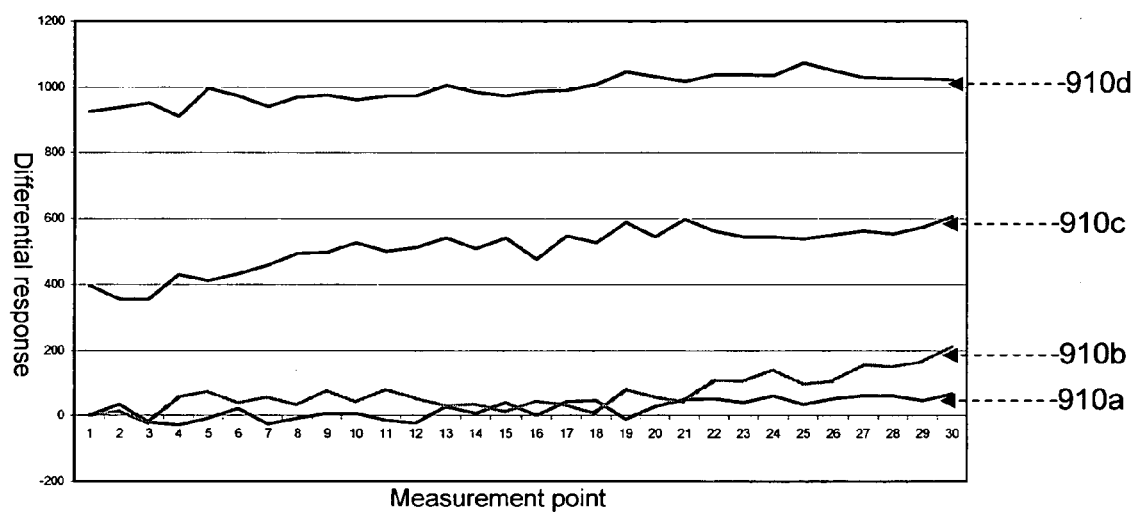
FIGS. 9A and 9B illustrate differential responses of TF-1 cells under different conditions using the monitoring system of FIG. 8.
Figure 9B:
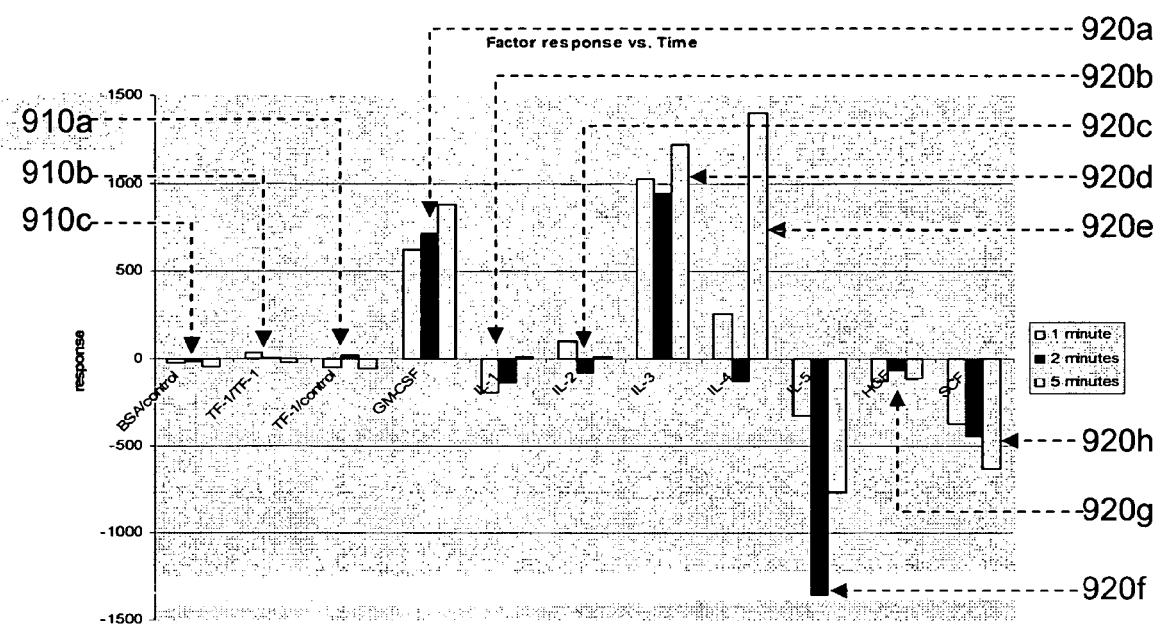

FIGS. 9A and 9B illustrate differential responses of TF-1 cells under different conditions using the monitoring system of FIG. 8. In one set of experiments the results of which are shown in FIG. 9A, a sequence of comparisons was carried out at an AC frequency of approximately 10 KHz, in which nearly identical populations of TF-1 cells at a concentration of about 2 million cells per milliliter of culture medium, were introduced into both channels. They were then followed for ten minutes, to establish a noise floor and a control response against which stimulated cells could be compared.

Response 910a in FIG. 9A depicts the response of the first control, in which TF-1 cells are placed in channels 800a and 800b of FIG. 8, and followed for thirty minutes. Next, a population of TF-1 cells, substantially similar to the control population, was prepared, and to one sample was added a quantity of GM-CSF (granulocyte-macrophage colony stimulating factor, which induces cell proliferation in TF-1 cells) in sufficient quantity to elicit the maximum response of the GM-CSF-mediated pathways. The other sample contained a nearly identical population of TF-1 cells, but without GM-CSF in the culture medium.

Responses 910b-d in FIG. 9A show the responses of the stimulated cells as compared to the control cells (response 910a), over a period of thirty minutes. Response 910b in FIG. 9A shows the response over the first ten minutes, when unstimulated TF-1 cells in one channel (800a in FIG. 8) are compared to TF-1 cells stimulated with GM-CSF in the other channel (800b in FIG. 8). Response 910c in FIG. 9A show the response over the second ten minute interval, and response 910d shows the response over the final ten minute interval. As can be seen, the stimulated cells show a change in the differential response over the control, and that change occurs over a time period beginning around eight minutes, and continuing to change in a nearly monotonic form for the remainder of the thirty minute experiment.

FIG. 9B illustrates a second set of experiments, in which the differential responses of a population of TF-1 cells against numerous stimuli and controls are shown at one minute, two minutes, and five minutes after stimulation. The test apparatus was substantially the same as that shown in FIG. 8. In these experiments, a population of TF-1 cells was fractionated into two portions of equal volume and cell density immediately before the experiment. One of the two fractions received a potential stimulus, and the other a control in the form of a quantity of pure Dulbecco's phosphate buffered saline (d-PBS)equal to the quantity of d-PBS which contained the stimulant. The control experiments include a direct comparison of nearly identical populations of TF-1 cells obtained directly from fractionating a larger quantity, a comparison of two fractions into which a solution containing an inert protein (BSA, or bovine serum albumin, a common plasma protein which is known not to affect TF-1 cells). Next, a series of factors and interleukins was compared against a reference sample. Each factor was introduced into one of two fractionated volumes containing TF-1 cells, via a 100:1 dilution of factor to d-PBS, followed by a 25 microliter addition of the diluted factor into approximately 200 microliters of the cell suspension. At the same time, the reference population of cells was prepared by adding 25 microliters of d-PBS alone into the second of the two cell fractions. Both fractions were then inserted into their respective channels in the apparatus, wherein said reference population was always inserted in the same channel, and measurements of the differential voltage were taken at pre-defined intervals over a five minute period. After each experiment, both channels were flushed with ~2 ml of cell-free culture media, to insure that all previous cellular material and any other potential compounds from a given experiment were removed from the channel before the subsequent experiment.

FIG. 9B shows the extent of the differential response for three controls at one minute, two minutes, and five minutes. Response 920a shows the response due to the activities of TF-1 cells to GM-CSF, and responses 920b-f show the responses of various interleukins (IL-1, IL-2, IL3, IL-4, IL5, and IL-6) on a population of TF-1 cells, also at one, two, and five minutes. The response to two other factors, HCF and SCF, both growth factors, are shown as responses 920g-h. TF-cells are known to support the activities of GM-CSF, IL3, IL4, and IL5, whereas IL-1 and IL-2 are known not to have any significant activities against TF-1 cells. This is reflected by the responses 920a and 920d-f, which show a significantly larger differential response over the three controls.

While the above is a detailed description of certain embodiments of the present invention, it is only exemplary and various modifications, alterations and equivalents may be employed in various apparatuses and processes described herein. Accordingly, the scope of the present invention is hereby defined by the metes and bounds of the following claims:

What is claimed is:

1. A system operable to monitor one or more bio/chemical activities within a first sample relative to a second sample, the system comprising:

a first measurement probe and a first reference element coupled to the first measurement probe, the first measurement probe operable to interrogate one or more physical properties of a first sample at a first location of the first sample, and to output, in response, a first measurement signal;

a second measurement probe and a second reference element coupled to the second measurement probe, the second measurement probe operable to interrogate one or more physical properties of a second sample at a first location of the second sample, and to output, in response, a second measurement signal;

wherein the first measurement probe, the first reference element, the second measurement probe, and the second reference element comprise are coupled together in a bridge circuit configuration, and a comparator coupled to receive the first and second measurement signals, the comparator configured to output a difference signal comprising the difference between the first and second measurement signals, the difference signal corresponding to the difference in one or more bio/chemical activities occurring within the first sample at the first location thereof relative to the second sample at the first location thereof, wherein the comparator includes:

a first differential amplifier having a first input coupled to the first measurement probe, a second input coupled to the first reference element, and an output;

a second differential amplifier having a first input coupled to the second measurement probe, a second input coupled to the second reference element, and an output; and a third differential amplifier having a first input coupled to the output of the first differential amplifier, a second input coupled to the output of the second differential amplifier, and an output for providing the difference signal.

2. The system of claim 1, wherein the first sample is a test sample containing or believed to contain one or more predetermined bio/chemical activities, and wherein the second sample comprises a reference sample which is known to contain one or more of the predetermined bio/chemical activities, wherein when the difference signal is within a predetermined range, the test sample is determined as comprising substantially the same one or more bio/chemical activities as the reference sample.

3. The system of claim 1, wherein the first and second measurement probes are operable to interrogate the first and second sample's electrical properties at respective first locations of each sample.

4. The system of claim 1, wherein the first and second measurement probes are operable to interrogate the first and second sample's optical properties at respective first locations of each sample.

5. The system of claim 1, wherein the first and second measurement probes are operable to interrogate the first and second sample's mass properties.

6. The system of claim 1, wherein the first and second measurement probes are operable to interrogate the first and second sample's chemical properties at respective first locations of each sample.

7. The system of claim 1, wherein the first and second measurement probes are operable to interrogate the first and second sample's mass and charge properties at respective first locations of each sample.

8. The system of claim 1, wherein the first and second measurement signals are non-DC formatted signals, the system further comprising a DC converter configured to convert the first and second measurement signals to respective DC formatted signals.

9. The system of claim 1, wherein the first and second measurement signals comprise DC formatted signals, wherein the difference signal comprises a DC formatted signal at a voltage level which corresponds to the difference between the first and second measurement signals.

10. The system of claim 1, further comprising a correlator having an input coupled to receive the difference signal, and memory operable to retain one or more stored difference signals, each stored difference signal corresponding to a predetermined bio/chemical activity, wherein the correlator compares the difference signal against one or more of the stored difference signals and identifies as occurring with the sample, the bio/chemical activity of the stored difference signal which has the closest correlation to the difference signal.

11. The system of claim 1, wherein the first and second reference elements comprise resistors.

12. The system of claim 1, wherein:
the first reference element comprises a third measurement probe, the third measurement probe operable to interrogate one or more physical properties of the first sample at the second location of the first sample, and to output, in response, a third measurement signal; and
the second reference element comprises a fourth measurement probe, the fourth measurement probe operable to interrogate one or more physical properties of the second sample at the second location of the second sample, and to output, in response, a fourth measurement signal.

13. The system of claim 1, wherein the comparator further comprises a phase meter having a first input coupled to the output of the first differential amplifier, and a second input coupled to the output of the second differential amplifier, the phase meter operable to output the relative phase difference between the first and second differential amplifier outputs.

14. The system of claim 11, further comprising a first signal ground proximate to the first measurement probe, wherein the first measurement probe is operable to interrogate the sample by transmitting a signal between the first measurement probe and the first signal ground.

15. The system of claim 14, further comprising a second signal ground proximate to the second measurement probe, wherein the second measurement probe is operable to interrogate the sample by transmitting a signal between the second measurement probe and the second signal ground.

* * * * *